(12) United States Patent
Schenker et al.

(10) Patent No.: US 10,413,673 B2
(45) Date of Patent: Sep. 17, 2019

(54) INJECTION DEVICE HAVING AN ACTUATING KNOB, THE ACTUATION OF WHICH EFFECTS A ROTARY MOVEMENT

(71) Applicant: TecPharma Licensing AG, Burgdorf (CH)

(72) Inventors: Susanne Schenker, Langenthal (CH); Ursina Streit, Schonbuhl (CH); Juerg Hirschel, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 627 days.

(21) Appl. No.: 15/062,910

(22) Filed: Mar. 7, 2016

(65) Prior Publication Data

US 2016/0184530 A1  Jun. 30, 2016

Related U.S. Application Data

(63) Continuation of application No. PCT/EP2013/068647, filed on Sep. 9, 2013.

(51) Int. Cl.
*A61M 5/315* (2006.01)
*A61M 5/20* (2006.01)

(52) U.S. Cl.
CPC .......... *A61M 5/31551* (2013.01); *A61M 5/20* (2013.01); *A61M 5/3155* (2013.01); *A61M 5/31583* (2013.01)

(58) Field of Classification Search
CPC .. A61M 5/31551; A61M 5/20; A61M 5/3155; A61M 5/31583; A61M 5/31591
See application file for complete search history.

(56) References Cited

U.S. PATENT DOCUMENTS

| 2012/0197213 A1* | 8/2012 | Kohlbrenner | A61M 5/20 604/220 |
| 2016/0074588 A1* | 3/2016 | Butler | A61M 5/20 604/211 |

FOREIGN PATENT DOCUMENTS

| CH | 705 155 | 11/2012 |
| EP | 2644217 | 10/2013 |
| WO | WO 2001/019434 | 3/2001 |
| WO | WO 2001/072361 | 10/2001 |
| WO | WO 2002/092153 | 11/2002 |
| WO | WO 2008/031237 | 3/2008 |

(Continued)

OTHER PUBLICATIONS

Compression springs (Lee Spring Feb. 7, 2019) (Year: 2019).*

(Continued)

*Primary Examiner* — Laura A Bouchelle
*Assistant Examiner* — Dung T Ulsh
(74) *Attorney, Agent, or Firm* — Dorsey & Whitney LLP

(57) ABSTRACT

The invention relates to a driving device for an injection device for administration of a liquid drug. The driving device has inter alia a rotary member, rotation of which relative to the housing causes a pretensioned spring to move a propulsion member in the dispensing direction, and a coupling which is closed and is opened by pressing of an actuating member, the opened coupling enabling the rotation of the rotary member in a first direction of rotation, and the actuating member being coupled to the rotary member such that pressing of the actuating member causes the rotary member to rotate already when the coupling is still closed.

23 Claims, 11 Drawing Sheets

(56) References Cited

FOREIGN PATENT DOCUMENTS

| WO | WO 2010/149209 | 12/2010 |
|----|----------------|---------|
| WO | WO 2013/119132 | 8/2013  |

OTHER PUBLICATIONS

International Search Report dated Oct. 24, 2014 for PCT/EP2013/068647 filed Sep. 9, 2013.
International Preliminary Report on Patentability dated Mar. 24, 2016 for PCT/EP2013/068647 filed Sep. 9, 2013.

* cited by examiner

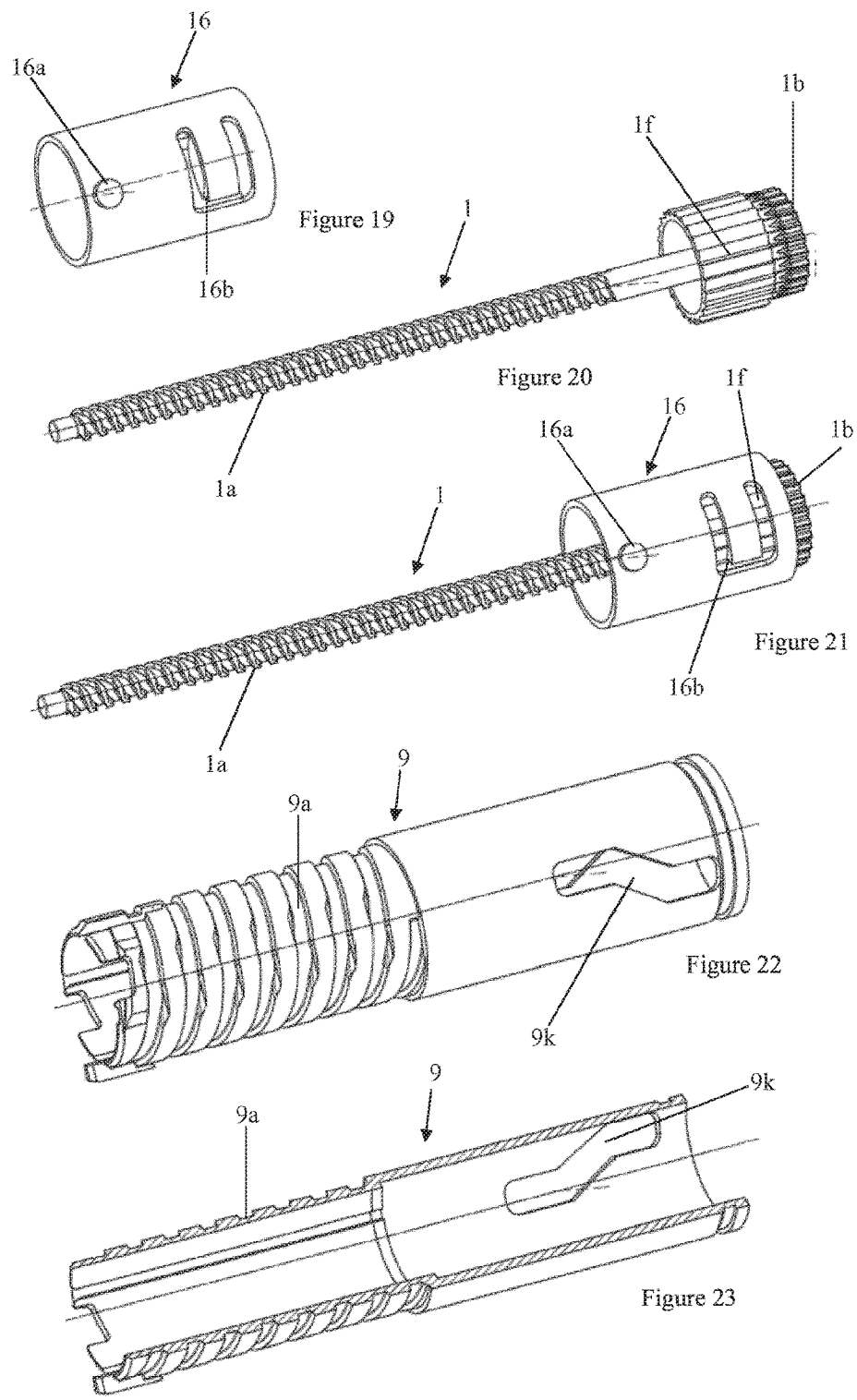

INJECTION DEVICE HAVING AN ACTUATING KNOB, THE ACTUATION OF WHICH EFFECTS A ROTARY MOVEMENT

CROSS-REFERENCE TO RELATED APPLICATIONS

This application is a Continuation of International Patent Application No. PCT/EP2013/068647 filed Sep. 9, 2013, the contents of which are incorporated herein by reference.

TECHNICAL FIELD

The invention belongs to the field of injection devices for administering a liquid product, particularly a medicine, such as insulin for diabetes therapy. The invention relates to a driving device such as a driving and dosing device for such an injection device.

BACKGROUND

An injection device having a dose indicating drum and a drive spring is known from the prior art, namely WO 2008/031237 A1. The drive spring is a coiled spring, which is wound in a spiral shape from a strip-shaped material. When the product dose is being set, the spring is cocked with a rotary movement. In order to dispense a dose, a piston rod is coupled to the spring by means of an actuating knob at the proximal end of the device, whereby the spring can output the energy stored therein to the piston rod, whereby the piston rod is moved in the dispensing direction. To set a new dose, the spring is again cocked by rotating the dosing knob, and so on. This is repeated until the product container has been emptied.

European Patent Application No. 12 162 777.2 describes a driving and dosing device as shown in the attached FIGS. 1-5c. This device has a drive spring, which is preloaded with sufficient energy in the delivery state of the driving and dosing device that it can dispense the dispensable quantity of product from the product container in multiple individual dispensing strokes. The dispensing spring drives a rotary member, the rotation of which causes a propulsion member to displace the piston of a product container, whereby the product contained in the product container is dispensed. To dispense the product, a pushbutton is actuated, whereby a closed clutch is opened, the opened clutch allowing the rotation of the rotary member and the closed clutch not allowing the rotation of the rotary member.

Such injection devices presume that the preloaded dispensing spring starts the dispensing of the product without further effort when the actuating knob or pushbutton has been completely actuated. Since such injection devices are occasionally stored for a long time prior to use, it is possible for the mechanism to become "stuck" or not properly release when the actuating knob has been completely actuated, so that dispensing of the product starts with a delay or only starts when a slight tap (mechanical shock) is applied to the injection device.

SUMMARY

A problem addressed by the invention is that of specifying an injection device that ensures that the dispensing of the product will start when the actuating knob has been actuated.

This problem is solved by the features of the claims, the description and the figures.

The invention proceeds from a driving device, more particularly a driving and dosing device, for an injection device for administering a liquid medicine or product. A fixed or invariable dose can be dispensed by using the driving device, or a dose can be set and subsequently dispensed. To the extent that the driving device allows the setting of a variable dose, for example by rotating a dosing element that can be gripped by the user, it can also be referred to as a driving and dosing device.

The drive device has a housing. The housing is preferably sleeve-shaped and/or elongated in shape. The housing can extend along a longitudinal axis, for example.

The housing can optionally accommodate a product container or can itself constitute the product container. The housing can be in one or more parts. For example, the housing can form a proximal housing part that comprises or has the driving device. The housing can additionally have a product container holder, which receives the product container, such as a carpoule, and is connected to the housing or the proximal housing part. This connection can be such that the product container holder and the housing or the proximal housing part is non-detachable after connection, i.e., only detachable by destroying connecting elements. Such an embodiment is particularly advantageous for single-use injection devices, which can be disposed of as a whole after the product contained in the product container has been completely dispensed. Alternatively, the product container holder can also be detachably connected to the housing, whereby it is possible to use the driving device several times if necessary, i.e., to replace an empty product container with a filled product container.

The housing is principally used in order to be gripped by the user of the device. In particular, the housing can have a substantially cylindrical shape. The housing can have a viewing device, particularly a window, by means of which or through which the currently set dosage can be read off, preferably from a scale of the dose setting element.

The driving device can comprise a propulsion member, the distal end of which is provided to act on a piston, in particular indirectly or preferably directly. The piston can be part of a product container such as a carpoule mounted or mountable on the driving device. In a broader sense, the propulsion member can be considered a piston rod, wherein the propulsion member need not necessarily be solid, but can also be hollow, e.g., sleeve-shaped. A flange, rotatable for example, which presses against the piston, can optionally be arranged at the distal end of the propulsion member. It is generally preferred that the distal end of the propulsion member presses against the piston. The propulsion member is preferably displaceable relative to the housing along the longitudinal axis of the driving device.

The driving device can have an abutment and preferably a guide, wherein the propulsion member is displaceable relative to the abutment and preferably also relative to the guide in one direction, more particularly the distal direction, i.e., the dispensing direction, in order to bring about a dispensing of the product, or optionally, of a setting product dose. The propulsion member can preferably be moved by means of or on the guide along the longitudinal axis of the driving device in a straight line or axially. In particular, the propulsion member can be rotationally fixed relative to the abutment or/and the guide or/and the housing. In an alternative embodiment, the propulsion member can be rotatable relative to the abutment or the housing combined with a longitudinal movement, i.e., screwable relative to the abutment. In general, the guide or/and the abutment can be formed from the housing, particularly a sleeve-shaped housing part or a sleeve-shaped element fixed relative to the housing, for example.

The propulsion member and the guide, formed in particular by the housing, can be in an engagement that prevents a rotation of the propulsion member relative to the abutment or the housing, and allows an axial movement or a helical movement of the propulsion member relative to the abutment or the housing. The guide can be an axial guide or a thread with a non-self-locking thread pitch.

The guide or the housing section, more particularly an inner sleeve that forms the abutment or/and the guide, can preferably surround the propulsion member, in a sleeve-like manner, and/or can be fixed relative to the housing or formed by the housing. An annular gap can be formed between this sleeve-shaped housing part and an external, preferably also sleeve-shaped, housing part, which brings the advantage that an optionally present dose-indicating element, particularly a dose-indicating drum, can be received therein, movably for example. The result is that the length of the driving device can be kept small.

The driving device can have at least one, e.g. exactly one, two or three, dispensing springs acting between the propulsion member or a rotary member and the abutment, and in particular arranged between them. The at least one spring can be supported on the propulsion member and/or the abutment, for example. The single dispensing spring, for example, can be supported at its distal end on the propulsion member, and at its proximal end, on the abutment. In particular, the at least one dispensing spring can be arranged inside the guide or the sleeve-shaped housing part forming the guide. If the propulsion member is sleeve-shaped, the at least one dispensing spring can be arranged inside the propulsion member. Alternatively, a first dispensing spring and a second dispensing spring can be arranged kinematically between the propulsion member and the guide or the sleeve-shaped housing part forming the guide. The first dispensing spring can surround the second dispensing spring, for example, or vice versa. In particular, the second dispensing spring can be arranged concentrically with the first dispensing spring. The first dispensing spring and the second dispensing spring can be connected in parallel or in series, for example. Springs connected in parallel means in particular that the first and the second dispensing springs are each supported at their distal end on the propulsion member and on the abutment at their proximal end. Thereby the spring constants of the first and second dispensing springs can be added up to a total spring constant. Springs connected in series means in particular that the distal end of either the first or the second dispensing spring is braced against the proximal end of the other of the first and second dispensing springs, particularly directly or preferably indirectly, e.g., via an intermediate element. For example, the first dispensing spring can be supported on the abutment and the intermediate element, and the second dispensing spring can be supported on the intermediate element and the propulsion member. The distal end of the first dispensing spring can be arranged distal to the proximal end of the second dispensing spring, for instance. Due to the intermediate element, the spring force of the first spring can be transmitted from its distal end onto the proximal end of the second dispensing spring. In particular, the intermediate element can be sleeve-shaped and arranged in an annular gap between the first and second dispensing springs. Springs connected in series make it possible to have a spring force that remains equal over a relatively long spring travel.

For example, the at least one dispensing spring, more particularly the first and second dispensing springs, can be a coil or helical spring that acts as a compression spring or torsion spring. The at least one dispensing spring is preloaded and acts on the propulsion member in such a manner that it attempts to displace the propulsion member in the distal direction, i.e., dispensing direction, relative to the abutment. The at least one dispensing spring is preloaded with sufficient energy in the delivery state of the driving and dosing device that it can dispense the maximum or total quantity of injectable product in the product container in multiple individual dispensing strokes, i.e., in multiple dispensing strokes of individual product doses.

If a dose can be set by the driving device, it can be designed such that the next dose to be dispensed is set after each individual dispensing stroke, or dispensing of the product dose. The driving device can have a dosing element, which can be formed as a dosing knob, for example, and can optionally be referred to as a dose-setting element. In contrast to embodiments in which a dispensing spring must be re-cocked for every dose adjustment, easier dose adjustment can be achieved with the spring cocked to the energy required for dispensing the maximum product quantity injectable from the product container, since the dosing element, which is rotatable relative to the housing for setting the dose, is then easier to rotate because the spring does not need to be cocked while setting the dose. This increases the convenience of using the device.

The driving device can additionally comprise a rotary member, the rotation of which has the effect that the spring outputs energy to the propulsion member, whereby the propulsion member is moved in the distal direction. The rotary member preferably takes on the function of a control member, wherein the rotation of the rotary member by a defined angle of rotation causes the advancement of the propulsion member by a defined dispensing stroke. By selectively releasing or blocking rotation of the rotary member relative to the housing, the spring can be allowed to move the propulsion member in the distal direction relative to the abutment, or not to move it. In particular, the rotary member can be coupled to the actuating member such that, upon actuation of the actuating member for dispensing of the product, the rotary member is released for a rotation relative to the housing in order to dispense the product, and it is blocked from rotation relative to the housing if the actuating member is not actuated. In particular, a clutch, more particularly a dispensing clutch, which effects the release and blocking of rotation of the rotary member relative to the housing, can be arranged between the actuating member and the rotary member. The closed clutch can be opened by actuating, more particularly pressing, the actuating member, wherein the opened clutch enables rotation of the rotation means, in particular the dispensing spring, relative to the housing, which can be effected by means of a preloaded spring.

The clutch can advantageously release the rotation of the rotary member relative to the housing if the actuating member is actuated and can block the rotation of the rotary member relative to the housing when the actuating member is released.

The actuating member is coupled to the rotary member in such a manner that actuating, more particularly pressing, the actuating member enables the rotary member to rotate relative to the housing if the clutch is still closed. The actuating member is displaceable between a non-actuated, i.e., non-pressed position and an actuated, i.e., pressed position in particular along the longitudinal axis of the driving device. The rotary member is rotated from the non-actuated into the actuated position by the displacement of the actuating member, already while the clutch is still closed. The non-actuated position can also be referred to as the starting position of the actuating member. The clutch is opened when the actuating member is in its actuated position. The actuating member is coupled to the rotary member via a transmission mechanism, which converts the movement along the longitudinal axis L, more particularly in the distal direction, into a rotary movement of the rotary member, more particularly in the first rotational direction. Rotating the rotary member even when the clutch is still closed has the advantageous effect that the parts that may have stuck together over time are released, more particularly by the user's muscular force, which presses the actuating member in the distal direction.

It is preferred that the rotation of the rotary member relative to the housing that is effected by the actuation of the actuating member while the clutch is closed is less than 45°, particularly less than 20°. The rotation of the rotary member relative to the housing that is effected by the actuation of the actuating member is preferably in the same rotational direction as the rotational direction of the rotary member that can be effected by means of the preloaded spring, more particularly in the first rotational direction, or alternatively in the opposite direction, more particularly the second rotational direction. The rotation of the rotary member that can be effected by means of the preloaded spring is in the first rotational direction.

In particular, the actuating member can be coupled to the rotary member in such a manner that the movement of the actuating member from its actuated position back into its non-actuated position, in particular the release of the actuating member, causes the rotary member to rotate relative to the housing in a direction of rotation, more particularly in the second rotational direction opposite the first rotational direction, the second rotational direction being opposite to the rotational direction, more particularly the first rotational direction, that can be effected by means of the preloaded spring. This effect can take place by means of the above-mentioned transmission mechanism. In particular, the actuating member can be moved back into its non-actuated position by a spring, more particularly a return or coupling spring, which is cocked by the actuation of the actuating member. Thereby this spring can turn the rotary member, more particularly via the transmission mechanism, in the second rotational direction.

Particularly, in embodiments in which the release of the actuating member causes the rotary member to rotate in the second rotational direction relative to the housing, it is preferred that the piston of the product container is displaced in the dispensing direction during dispensing of the product or during the rotation of the rotary member in the first rotational direction by the propulsion member acting on the piston, and that during movement of the actuating member back into its non-actuated position, the propulsion member is moved opposite to the dispensing direction relative to the abutment, in particular sufficiently far that the piston is relieved of the pressure from the propulsion member. The rotation of the rotary member in the second direction causes the propulsion member to be moved at least slightly in the proximal direction, i.e., contrary to the dispensing direction, so that the piston of the product container is relieved of pressure. The dispensing spring can also be relaxed somewhat. The clutch is preferably already closed when the propulsion member moves in the proximal direction.

The above-mentioned transmission can have a first transmission element and a second transmission element. A first part can form the first transmission element and a second part can form the second transmission element, wherein the first transmission element and the second transmission element slide along one another due to the actuation of the actuating member, whereby the actuation, more particularly the pressing of the actuating member, causes the rotary member to rotate relative to the housing, more particularly in the first rotation direction, already when the clutch is still closed.

In one embodiment, the housing or an element fixed to the housing can form the first part, and the second part can be, e.g., a sleeve-shaped displacement element that helps to form the clutch, more particularly a bearing element, which is displaceable at least axially in relation to the housing or the element fixed to the housing. The displacement element can be the element fixed to the housing. The first part and the second part can engage with one another in such a manner that a displacement of the second part that is effected by the actuating member brings about a rotation of the second part relative to the first part. Either the first part or the second part can be an engagement element and the other of the two parts has a guide track, wherein the movement of the engagement element in the guide track effects a rotation of the second part relative to the first part. For example, the guide track can be a thread or threaded section. The guide track, for instance, can have a proximal and/or a distal guide track section, which are connected via a transition section, or a transition section adjoins the proximal or distal guide track section. If the engagement element is moved in the guide track, particularly in or through the transition section, it can effect a rotation of the second part relative to the first part, more particularly in the first rotational direction when the actuating member is actuated, and the engagement element is moved in a first direction in the guide track or through or in the transition section, and in particular the engagement element can effect a rotation in the second rotation direction when the actuating member is released and the engagement element moves in a second direction, which is the opposite of the first direction, in the guide track or through or in the transition section. For example, the proximal guide track section and/or the distal guide track section can be parallel to the longitudinal axis, so that the second part is rotationally fixed and axially displaceable relative to the first part when the engagement element is in the proximal or the distal guide track section.

In another embodiment, the rotary member forming part of the clutch can be the first part and the second part can be a displacement element, particularly the bearing element, which forms part of the clutch and is rotationally fixed relative to the housing or to an element fixed to the housing and is movable along the longitudinal axis of the driving device. For example, the first part and the second part can slide along one another during the displacement of the second part, which is caused by the actuation or release of the actuating member, whereby the first part is rotated relative to the housing, more particularly in the first rotational direction, when the actuating member is actuated, and/or in the second rotational direction when the actuating member is released. The first part and the second part can engage with one another. For example, the first part can have protrusions that point to the second part and the second part can have protrusions that point to the first part. The protrusions facing and engaging with one another can slide along one another when the actuating member is actuated. The protrusions can be a part of the clutch structure of the aforementioned clutch, for example, wherein the clutch is only released if the protrusions that preferably face one another have slid along one another and disengaged. Thereby the rotary member can rotate in the first rotational direction relative to the housing and the second part by means of the preloaded dispensing spring.

In additional embodiments, the rotary member can have toothing or a plurality of teeth, e.g. sawtooth-shaped, arranged over its periphery, with which toothing or teeth a latching cam, which is formed from an intermediate sleeve arranged over the periphery of the rotary member, resiliently engages, wherein the intermediate sleeve is the first part and forms a clutch structure of the clutch, and the second part is a displacement element, more particularly a bearing element, which is rotationally fixed and axially displaceable in relation to the housing or an element fixed to the housing, wherein the preferably sleeve-shaped displacement element surrounds the intermediate sleeve around the periphery thereof. The intermediate sleeve can be arranged concentrically between the rotary member and the displacement element. For example, either the displacement element or the intermediate sleeve can have a protrusion, which engages with a guide track of the other of the two parts. For example, the guide track can be a thread or threaded section. The guide track, for instance, can have a proximal and/or a distal guide track section, which are connected via a transition section, or a transition section adjoins the proximal or distal guide track section. If the protrusion is moved in the guide track, particularly in the transition section, it can effect a rotation of the intermediate sleeve, and in particular the rotary member, relative to the displacement element, more particularly in the first rotational direction, when the actuating member is actuated and the protrusion is moved in a first direction in the guide track, particularly through or in the transition section; the intermediate sleeve can move in the second rotation direction when the actuating member is released and the protrusion moves in a second direction, which is the opposite of the first direction, in the guide track or particularly through or in the transition section. For example, the proximal guide track section and/or the distal guide track section can be parallel to the longitudinal axis, so that the intermediate sleeve is rotationally fixed and axially displaceable relative to the displacement element when the protrusion is in the proximal or the distal guide track section. The guide track and the protrusion engaging with the guide track advantageously cause the intermediate sleeve to rotate in the first rotational direction when the actuating member is actuated, i.e. displaced from its non-actuated position into its actuated position.

The engagement of the latching cam with the teeth arranged across the periphery is such that a rotation of the intermediate sleeve in a first direction relative to the rotary member is prevented and a rotation of the rotary member in the first direction relative to the intermediate sleeve is possible. The actuation of the actuating member causes a rotation of the intermediate sleeve in the first rotational direction relative to the housing, wherein the intermediate sleeve drives the rotary member, i.e., rotates with it. When the actuating member is in its actuated position, the drive spring can rotate the rotary member relative to the intermediate sleeve in the first direction, since the clutch has been opened. For example, the clutch element, in particular the bearing element or the inner surface thereof such as the inner periphery, can prevent the latching cam from being moved out of the toothing of the rotary member if the actuating member is non-actuated or not completely actuated, i.e., not in its actuated position. The displacement element, more particularly the bearing element, preferably enables the movement of the latching cam out of the toothing when the actuating member has been completely actuated, i.e., is in its actuated position. For this purpose, the displacement element can have a recess, which is pushed over the latching cam by means of the actuation of the actuating member, so that the latching cam can move out of engagement with the toothing. Alternatively or additionally, the inner surface of the displacement element, more particularly the bearing element, can be moved out of the position in which it holds the latching cam in engagement with the toothing, so that the latching cam can move out of the engagement with the toothing. Preferably, the latching cam moves out of engagement with the toothing approximately radially outward, i.e., away from the longitudinal axis, and moves approximately radially inward, i.e., toward the longitudinal axis, into engagement.

The dispensing spring is preferably arranged kinematically between the piston of the product container and the rotary member. In this way it is possible to prevent the dispensing energy provided by the dispensing spring from having to run largely via the rotary member, as would be the case if the rotary member were arranged kinematically between the dispensing spring and the piston. Thereby the rotary member can be designed more simply. In particular, this can cause the at least one dispensing spring to drive the propulsion member and the propulsion member to drive the rotary member. In particular, the propulsion member can be arranged kinetically between the dispensing spring and the rotary member.

In particular, the angle of rotation of the rotary member can be proportional to the dispensing stroke of the piston or the propulsion member. This can be achieved by selectively blocking or releasing the rotary member.

The rotary member can advantageously be in an engagement, particularly a threaded engagement, with the propulsion member. The thread pitch of this threaded engagement has the effect that, in the case of a complete revolution of the rotary member relative to the housing, the propulsion member can be displaced by the dispensing spring by an amount that corresponds to the thread pitch, for example.

The rotary member can be a threaded rod, for example, and the propulsion member can have or be a threaded nut, wherein the thread of the threaded nut engages with the thread of the threaded rod.

In an alternative example, the rotary member can be a threaded nut and the propulsion member can have or be a threaded rod, wherein the thread of the threaded nut engages with the thread of the threaded rod.

The rotary member is preferably axially fixed in relation to the housing, or can at least be supported axially fixedly in one direction, preferably the distal direction, on the housing, or to an element fixed to the housing such as the abutment.

It is advantageous that the rotary member is connected rotationally fixedly to the housing during the setting of a dose, i.e., in the non-actuated state, by means of the clutch in particular, and is rotated or rotatable relative to the housing during the actuation of the device to dispense the product dose.

In embodiments in which a product dose is adjustable, the driving and dosing device has a dose indicating element, in particular a dose indicating drum. The dose indicating element can be in a threaded engagement with the housing or an element fixed to the housing for example, whereby the dose indicating element can be screwed along the housing by rotating a dose setting element. Alternatively, the dose-indicating element can be in a threaded engagement with the displacement element, in particular the bearing element.

The dose indicating element, particularly the dose indicating drum, can be rotatable relative to the rotary member during the setting of a dose, i.e., in the non-actuated state of the driving and dosing device or the actuating member. The dose indicating element is preferably rotationally fixed relative to the rotary member during the actuation of the device in order to dispense the product dose and is axially movable, for example, or is rotationally fixedly connected to the rotary member, in particular via the above-described clutch or some other clutch.

This has the advantageous effect that during dispensing of the dose, i.e., when the actuating member is in its actuated position, the dispensing spring screws the dose indicating element back into its zero dose position, particularly via the rotary member and preferably via a clutch element, which is preferably arranged rotationally fixedly but axially displaceably in relation to the dose indicating element. In particular, the clutch element and the dose indicating element can be in a rotationally fixed engagement that allows an axial movement between the dose indicating element and the clutch element. This engagement can be effected by means of a longitudinal guide, for example. The clutch element is preferably axially fixedly but rotatably connected to the displacement element, more particularly the bearing element.

For example, the driving and dosing device can have a first clutch structure that is rotationally fixed in relation to the housing. The rotary member can have or form a second clutch structure that, when in coupling engagement with the first clutch structure, causes the rotary member to be rotationally fixed in relation to the housing. The first clutch structure can be formed by the housing, for example, or by a displacement element such as the bearing element, which is arranged rotationally fixedly but axially displaceably in relation to the housing.

The clutch element can have a third clutch structure which, when engaged with the first clutch structure or an additional, fourth clutch structure of the rotary member, causes the dose indicating element to be rotationally fixedly connected to the rotary member. When the actuating member is in the non-actuated position, the rotary member and the housing are rotationally fixed to one another; in particular, the first and second clutch structures are engaged, while the third and second or optionally the third and fourth clutch structures are disengaged. If the actuating member is in its actuated position, the third and second, and optionally the third and fourth clutch structures are engaged, while the first and second clutch structures are disengaged from one another.

It is particularly advantageous if the dose indicating element is already rotationally fixedly coupled to the rotary member and the rotary member is still rotationally fixedly coupled to the housing while the actuating member is being pushed for actuation onto the housing. This ensures that the dose indicating element is first coupled securely to the rotary member when the rotary member has been released for a rotation relative to the housing. In other words, there is an intermediate position between the actuated and non-actuated position of the actuating member, in which the rotary member is coupled rotationally fixedly to both the housing and also to the dose indicating element. In particular, the first and the second and the third and the second clutch structures and optionally the third and the fourth clutch structures can be simultaneously engaged, namely when the actuating member occupies its intermediate position.

In generally preferred embodiments, the dose indicating element can have a stop, such as a zero dose stop, which is moved away from a mating stop, in particular a zero dose mating stop, whenever a dose is increased, and is moved toward the mating stop whenever a dose is reduced, or when the device is actuated for dispensing the set product dose.

In particular, the dose indicating element can be at least rotationally decoupled from the rotary member during setting of the product dose, i.e., dose increase and dose reduction and, during actuation of the device for dispensing the product dose, can be coupled with the rotary member in such a manner that a rotation of the rotary member has the effect of moving the dose indicating element toward the mating stop, i.e., the zero dose stop is moved toward the zero dose mating stop. If the zero dose stop and the zero dose mating stop are stopped or in contact, this prevents, particularly via the clutch, a rotation of the rotary member and thus prevents further advancement of the propulsion member relative to the housing.

Between the dose setting element and the dose indicating element, there can be a dosing clutch, which couples the dose setting element to the dose indicating element rotationally fixedly if the driving and dosing device or the actuating member is non-actuated, and rotationally decouples them if the driving and dosing device or the actuating member has been actuated. In other words, the dose indicating element and the dosing element are coupled rotationally fixedly via the dosing clutch whenever the actuating member is non-actuated, and the dose indicating element is rotatable relative to the dose setting element whenever the actuating member has been actuated. The dosing clutch is opened by actuation of the actuating member.

In advantageous refinements, the driving and dosing device can comprise a mechanism for preventing the setting of a dose that exceeds the quantity of a medication in the product container. In particular, this mechanism can block rotation of the dosing element in a direction that would cause an increase of the dose, more particularly even if the maximum stop of the dose indicating element and the maximum dose mating stop are not yet engaged or, if a dose is displayed in the viewing device that is smaller than the maximum adjustable product dose, for example. The mechanism thus prevents setting a dose that exceeds the remaining amount of product contained in the product container, which reduces the danger of misuse of the driving and dosing device. The mechanism can have a limiter, for example, which is positioned between two parts, one of which rotates relative to the other during dose-setting and does not rotate during actuation, i.e., dose dispensing. For example, the limiter can be arranged between the dose-setting element, which can be designed in particular as a dose-setting knob or dose-setting sleeve, and the housing or an element fixed in relation to the housing. The limiter, the dose-setting element and the housing can be coupled to one another in such a manner that a relative rotation, particularly during dose-setting, between the dose-setting element and the housing causes the limiter to move to a stop position in which the limiter prevents setting a dose that exceeds the amount of a product in the product container. Examples of appropriately suitable limiters are disclosed in WO 2010/149209 A1 or in WO 01/19434 A1, particularly in FIG. 3 thereof. For example, the limiter can have an internal thread that is engaged with an external thread of the housing. In particular, the limiter can have a longitudinal guide on its outer side by which it is engaged with the dose-setting element such that the dose-setting element is rotationally fixed relative to the limiter. Alternatively, the housing can have the longitudinal guide for the limiter, so that the limiter is rotationally fixed relative to the housing and the limiter can have a thread, particularly an external thread, that engages with a thread, particularly an internal thread, of the dose-setting element.

The stop position is defined by a stop for the limiter, wherein the stop can be formed by the housing or the dose-setting element or a means fixed relative to the housing at least axially or in the circumferential direction. If the limiter and the stop are in contact, a rotation of the dose-setting element in a direction that would cause an increase of the dose is no longer possible or is blocked.

In generally preferred refinements, the driving and dosing device can optionally have at least one signal generation mechanism, which is adapted to generate an acoustic and/or tactile signal, more particularly mechanically, during the dose-setting or/and dispensing of the product. Such a signal can be perceived as a click signal. For example a (first) signal generation mechanism can be provided, which generates the signal during the dose-setting and can optionally be referred to as a dose-setting signal generation mechanism. Alternatively or additionally, a (second) signal generation mechanism can be provided, which generates the signal during dispensing of the product and can optionally be referred to as a product dispensing signal generation mechanism. Alternatively, a (common) signal generation mechanism can be provided, which generates a signal during dose-setting and during dispensing of the product.

In general the signal generation mechanism can be arranged between two parts that move, more particularly rotate, relative to one another during dose-setting or/and dispensing of the product. One of the parts can have a resiliently arranged catch element, for example, which engages with toothing of the other one of the two parts, arranged across the periphery thereof, for example. If one part is moved relative to the other, the catch element can slide over the toothing and generate the signal. The toothing can be formed by an internal periphery or external periphery or an end face of the part. For example, the signal generation mechanism for dispensing of the product can be formed by the cam of the intermediate sleeve, which was described above in relation to one embodiment.

In particular, the signal generation mechanism can be formed between the clutch element and the displacement element or bearing element. The clutch element and the displacement element or bearing element preferably rotate relative to one another during dose-setting and dispensing of the product, whereby a signal generation mechanism is formed that generates the signal during dose-setting and dispensing of the product.

The signal generation mechanism can be formed in particular between the displacement element or bearing element and the rotary member, wherein that which was explained for the displacement element or bearing element applies here as well, at least in the present context, for a switching sleeve described herein. The displacement element or bearing element and the rotary member preferably rotate relative to one another during, more particularly only during, dispensing of the product, whereby a signal generation mechanism is formed that generates a signal during dispensing of the product.

The signal generation mechanism can be formed in particular between the clutch element and the rotary member. The clutch element and the rotary member preferably rotate relative to one another during, more particularly only during, dose-setting, whereby a signal generation mechanism is formed that generates a signal during dose-setting.

A dose scale can be arranged over the periphery of the dose indicating element. The dose indicating element can be annular in cross section, for example. The dose indicating element can be a dose indicating drum or a dose indicating ring, for example. The dose scale can extend, preferably in a helical shape, over the periphery of the dose-indicating element. The dose scale preferably comprises a plurality of values, which are arranged one after another and produce the dose scale. These are preferably numerical values that indicate the desired product dose in international units (IU).

Alternatively, the dose scale can be arranged without a pitch over the periphery of the dose indicating element, such as the dose indicating ring, in which case the scale values then repeat after a revolution of the dose indicating element. In a dose scale with a pitch, i.e. a helical dose scale, the dose indicating element, particularly the dose indicating drum, can be rotated more than one revolution without the scale values repeating, whereby higher or more scale values can advantageously be represented.

The driving and dosing device further comprises a viewing device, wherein the dose indicating element, in order to set the dose, can be rotated relative to the viewing device and particularly about a rotational axis that preferably corresponds to the longitudinal axis of the driving and dosing device or/and the dose indicating element. This movement can be a purely rotary movement, i.e. a rotary movement without superimposed axial movement. Preferably an axial movement is superimposed on the rotary movement, whereby the dose indicating element is screwable relative to the viewing device in order to set the dose to be administered. A screwable dose indicating element can advantageously be combined with a helical dose scale, the screwing movement and the dose scale preferably having the same pitch. A dose indicating element without axial movement can be advantageously combined with a pitch-free dose scale.

A value of the dose scale that corresponds to the set dose can be read out by means of the viewing device, which is preferably formed on the housing. The viewing device can be a window, for example, which can be formed by an opening in the housing or by a transparent insert. Alternatively or optionally, the viewing device can be an arrow or have an arrow, which marks the value of the dose scale corresponding to the set dose in addition to the window. This is advantageous if a second value appears in the window, at least partially, in order to ensure an unambiguous choice of dose, for example. The pointer can be a protrusion or an imprint or a notch or the like.

The dosing element can preferably be gripped by the user (patient, physician, medical assistance personnel) of the driving and dosing device and preferably constitutes an external, more particularly externally accessible, surface of the driving and dosing device. To set the dose to be dispensed or administered, the dosing element is preferably gripped by the user and rotated relative to the housing, and in particular to the viewing device, about an axis of rotation that preferably corresponds to the longitudinal axis of the driving and dosing device, which is designed in an elongated shape, for example. The dosing element is preferably connected axially fixedly to the housing, more particularly secured against displacement along a longitudinal axis of the housing, whereby the intuitive handling of the device by the user is advantageously facilitated, because the user needs only to carry out a rotary movement of the dosing element to adjust the dose.

In particular, the dose indicating element can be secured against rotation at least during the dose-setting, but connected or coupled to the dosing element so as to be axially displaceable, for example. For intuitive operation, it is advantageous if, when the dosing element is rotated by a given angle of rotation, the dose-indicating element is rotated by the same angle of rotation.

The actuating member, preferably designed as an actuating knob, can form an outer surface of the driving device and/or can be accessible from the outside. The actuating member can be formed on the proximal end, in particular the rear end, of the driving device, or can constitute this end. In this manner, the actuating member can advantageously be actuated, particularly pressed, with the thumb of the hand that is gripping the housing. The actuation can be ended by releasing the actuating member.

The actuating member can advantageously be displaceable, more particularly actuatable, against the force of a spring, particularly a return or coupling spring, whereby this spring is cocked. By being released, this spring can reset the actuating member, more particularly displace it relative to the dosing element, specifically in the proximal direction or out of the driving device.

The driving and dosing device can further comprise a bearing element, with which the dose indicating element is engaged. This engagement advantageously effects the rotary or screwing movement of the dose indicating element relative to the viewing device. For example, the engagement between the dose indicating element and the displacement element or bearing element can be a threaded engagement. In particular, the bearing element can have an external thread and the dose indicating element an internal thread, these threads engaging with one another and thereby causing the dose indicating element to be screwable relative to the bearing element.

The dose indicating element can be rotated or screwed between a maximum dose position and a zero dose position. In the zero dose position, the dose or the digit "0" can advantageously be readable in the viewing device. In the maximum dose position, the maximum product dose that can be dispensed with the driving and dosing device can advantageously be readable.

The dose indicating element can be blocked in the zero dose position against rotation in one rotational direction, namely the rotational direction that would cause a dose of less than zero to be set. In the zero position, the display element can preferably only be rotated in a direction of rotation that causes an increase of the dose. In the maximum dose position, the dose indicating element is preferably blocked against rotation in one rotational direction, namely the rotational direction that would cause the setting of a dose greater than the maximum settable dose. Preferably, the dose indicating element in the maximum dose position can only be rotated in the direction that causes a reduction of the product dose.

For example, the dose indicating element can have a stop that strikes against a mating stop in the zero dose position and thus prevents rotation in one rotational direction. The same or an additional stop on the dose indicating element can prevent rotation of the dose indicating element past the maximum dose. In particular, an additional mating stop, namely a maximum dose mating stop, can be provided for this purpose. The other mating stop can accordingly be referred to as the zero dose mating stop. Thus the dose indicating element can have a zero dose stop for the zero dose mating stop and a maximum dose stop for the maximum dose mating stop. The stop or the stops preferably act in the circumferential direction and/or in the axial direction.

The bearing element can be displaced together with the dose indicating element relative to the housing and along the axis of rotation, more particularly in the distal direction. Alternatively, the dose indicating element can have a thread that is engaged with the housing. Thereby the dose indicating element can be displaced back and forth relative to the housing but not independently of the screwing movement, particularly not with a purely axial movement.

The actuating member is preferably coupled to the bearing element in such a manner that a displacement of the actuating member relative to the housing and/or the dose-setting element causes a displacement of the bearing element relative to the housing and/or the dose-setting element, particularly along the longitudinal axis of the driving and dosing device.

Because the dose indicating element is engaged with the bearing element and the bearing element can be displaced relative to the housing and along the axis of rotation, the dose indicating element can also be displaced relative to the housing and along the axis of rotation independently of the rotating or screwing movement that the dose indicating element undergoes during setting of the dose. The driving and dosing device can basically also be combined advantageously with the alternative dose indicating element, which is in threaded engagement with the housing or an element fixed relative to the housing. In this alternative, the bearing element can be formed by the housing or be a part of the housing, wherein the bearing element can then be secured rotationally and axially in relation to the remainder of the housing. The displacement element and the bearing element are then separate parts.

The fact that the bearing element has been displaced together with the dose indicating element can advantageously be read out on the viewing device or the dose indicating element. In this way, the user can monitor the operating status of the driving and dosing device, i.e. whether the driving and dosing device, and in particular the actuating member, is or is not actuated for dispensing.

In a preferred variant, the actuating member or/and the bearing element can be displaceable, together with the dose indicating element, relative to the viewing device and the housing, along the axis of rotation. In the area of the viewing device, particularly in the window of the viewing device, a mark different from the dose scale can appear when the bearing element has been displaced. The mark is preferably arranged on the dose indicating element. If the bearing element has not been displaced, more particularly if the driving and dosing device has not been actuated for dispensing the product, the mark can be arranged outside the viewing device, for example concealed by a housing or some other element. If the bearing element has been displaced, in particular if the driving and dosing device has been actuated for dispensing the product, the mark can emerge from the covered area, so that it appears or is readable on or in the viewing device. If the actuation of the driving and dosing device has been interrupted or terminated, the bearing element can return to the original position, whereby the mark preferably is removed from the area of the viewing device and in particular is concealed.

In an alternative variant, the actuating member or/and the bearing element can be displaceable together with the dose indicating element and the viewing device relative to the housing and along the axis of rotation. The viewing device can be a screen, for example, or at least perform the function of a screen. For example, the viewing device can be connected to the bearing element at least axially fixedly, preferably also rotationally fixedly. The bearing element can basically form the viewing device. It is of course also possible for the viewing device to be a part separate from the bearing element. The viewing device can be sleeve-shaped, for example.

In this variant, the displacement of the bearing element can cause a mark, which is arranged or formed alongside or on top of the viewing device and differs from the dose scale, to appear in the area of the viewing device. For example, the viewing device can be arranged inside the housing. The mark of the viewing device can be concealed by the housing or another element in the non-actuated state of the driving and dosing device. If the driving and dosing device, more particularly the actuating member, is actuated and thus the dose indicating element is displaced together with the viewing device, the mark can emerge from its covering, so that the mark is visible or readable. If the actuation is interrupted or terminated, the dose indicating element, together with the viewing device and the bearing element, can be displaced back into its initial position and therefore the mark is again arranged under the cover.

It is generally preferred that a spring, particularly a coupling or return spring, is cocked during the actuation of the driving device for dispensing a product. For example, the bearing element can be displaced during actuation against the force of the spring, particularly a spring of this type, from a non-actuated position into an actuated position. The spring can be a helical spring or a coil spring, for example, acting as a compression spring. This spring has the further effect of resetting the bearing element to the starting position or non-actuated position if the actuation is interrupted or ended. In particular, the bearing element is displaced in the distal direction during actuation. The bearing element is pushed back into its original position by means of the spring if the actuation is interrupted or ended.

Actuating the actuating member has the effect in particular of displacing the bearing element together with the dose indicating element relative to the housing and along the axis of rotation.

The actuating member is preferably connected to the displacement element or bearing element in such a manner that it displaces the bearing element during actuation, more particularly via a clutch element which can be connected axially fixedly and rotatably to the bearing element, for example.

In generally preferred embodiments, the actuation of the actuating member can cause the dose indicating element to be rotated, particularly screwed, relative to or on the bearing element or the housing, more particularly in a direction such that the values moving past the viewing device during the rotary movement count down on the dose scale. The angle of rotation of the dose indicating element and the dispensing stroke of the propulsion member preferably have a proportional relationship, more particularly at every point during the dose dispensing. This makes it possible to implement a real-time display that counts down during dose dispensing until it finally reaches the value 0, at which point the dispensing of the dose in question is complete. If the actuation for dispensing is interrupted during the back-rotation of the dose indicating element, the dose indicating element indicates the remaining amount necessary for the dispensing of this dose.

In a preferred alternative variant, the driving and dosing device can be designed such that the energy required for the back-rotation of the dose indicating element or/and the displacement of the propulsion member in the distal direction is exerted automatically, more particularly by means of a spring, in particular a dispensing spring, in which the required energy is or can be stored. For example, the spring energy stored in the dispensing spring can be output to the dose indicating element or/and the propulsion member upon actuation of the actuating member so that the dose indicating element is rotated back and the propulsion member is displaced in the distal direction.

The spring can already be cocked with sufficient energy upon delivery of the driving and dosing device that the energy suffices for several dispensing strokes of the product dose, in particular for dispensing the entire product that can be dispensed from the product container. In this embodiment, the dosing element can be decoupled from the spring during dose-setting, i.e. not coupled to the dispensing spring in such a manner that a rotation of the dosing element cocks the spring. In this manner the dosing element can be rotated by the user to set the dose with considerably less force exertion.

The dosing element, more particularly the dosing knob, can surround or receive the actuating member, specifically the actuating knob. Thus the dosing element and the actuating member can form the proximal end of the driving and dosing device. The actuating member is preferably displaceable relative to the dosing element for actuation.

In particular, the dosing element can be arranged axially fixedly on the housing and rotatable.

BRIEF DESCRIPTION OF THE DRAWINGS

FIGS. 2a-c show the driving and dosing device from FIG. 1 in an initial or delivery state, wherein FIG. 2b is a sectional view of FIG. 2a and FIG. 2c is a sectional view of FIG. 2a rotated by 90° along the line B-B, FIGS. 15-23 show various views of a third embodiment of the invention.

DETAILED DESCRIPTION

Figure 1:
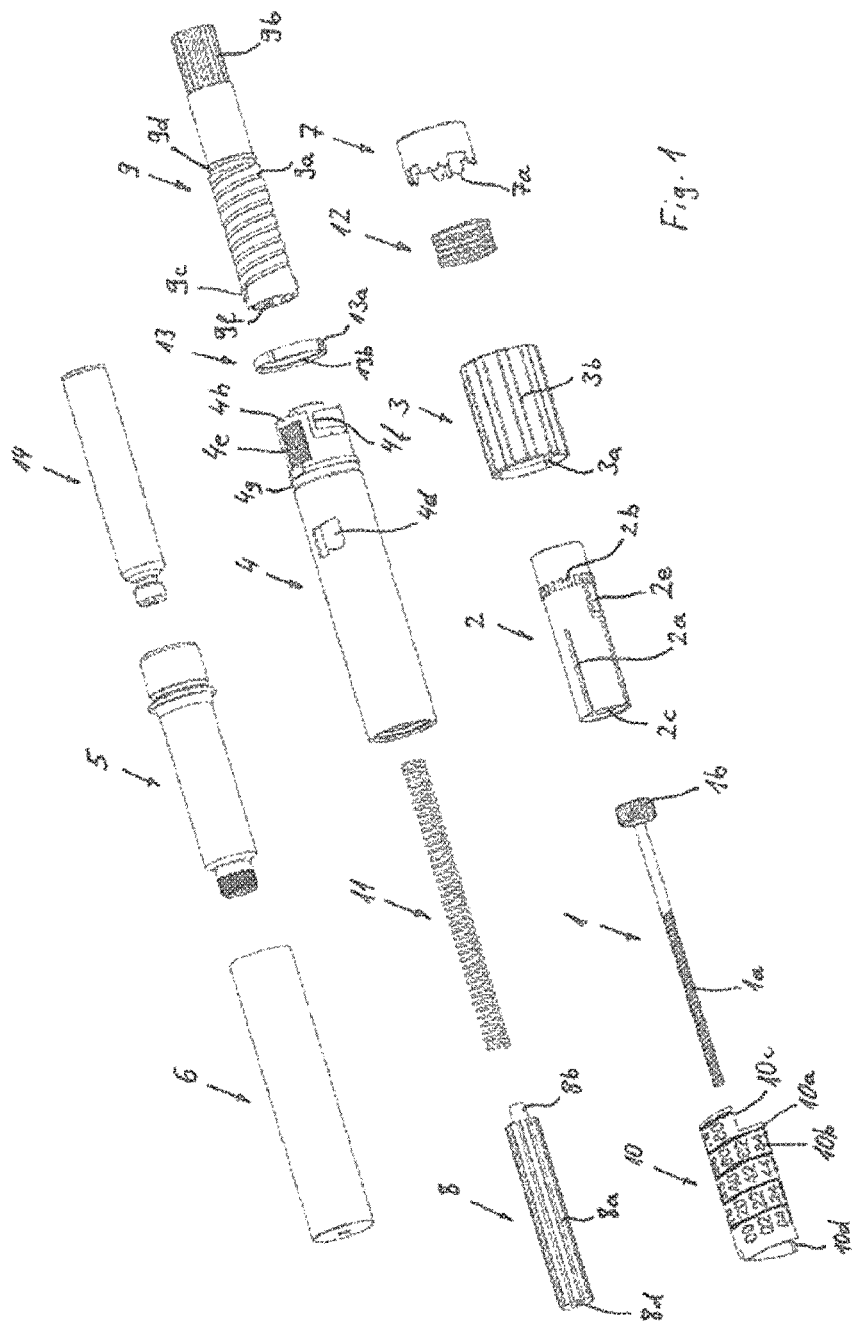
FIG. 1 shows an exploded view of an example of a driving and dosing device that can advantageously be used in connection with embodiments of the invention.
Figure 2:
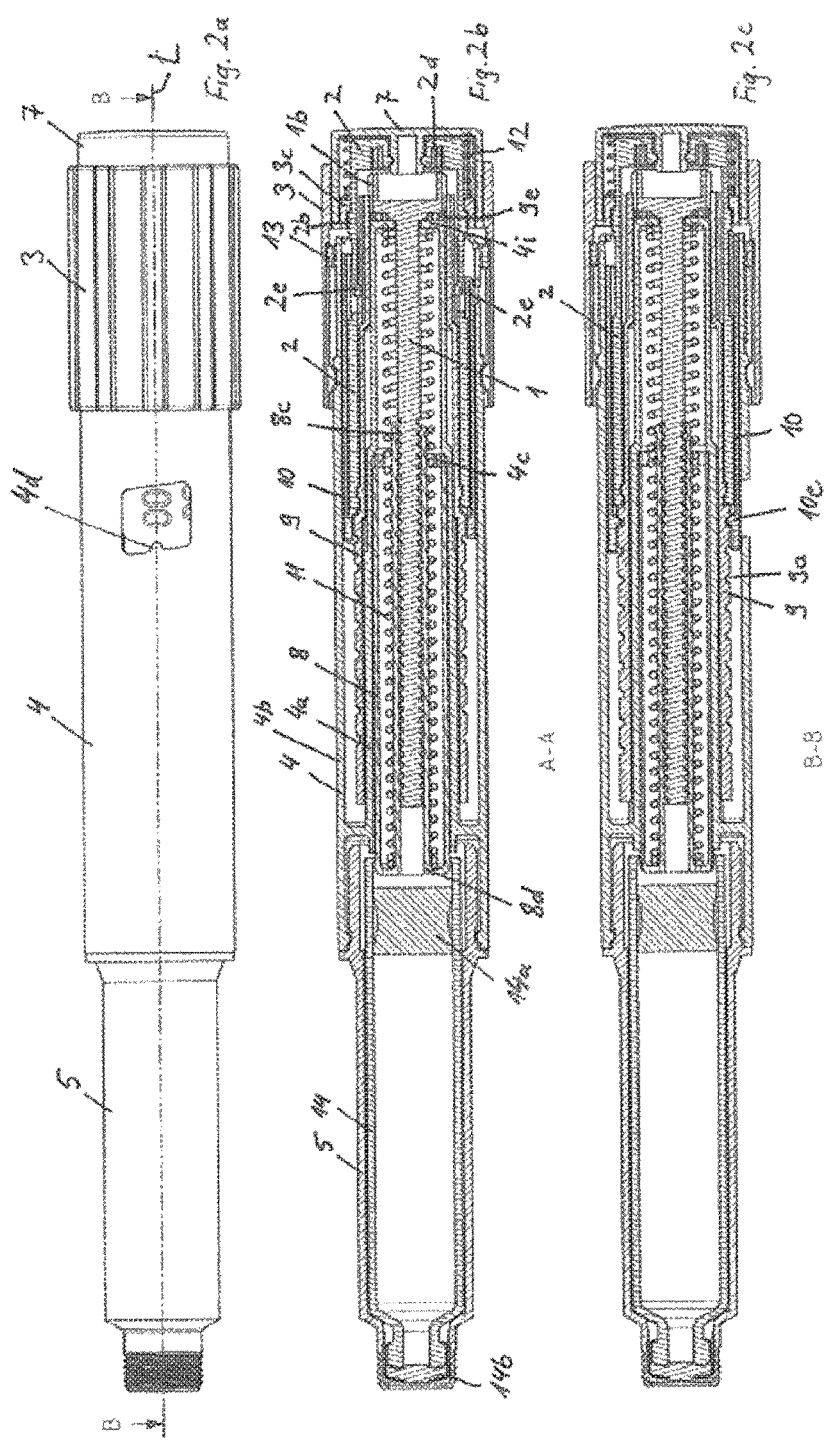
Figure 3:
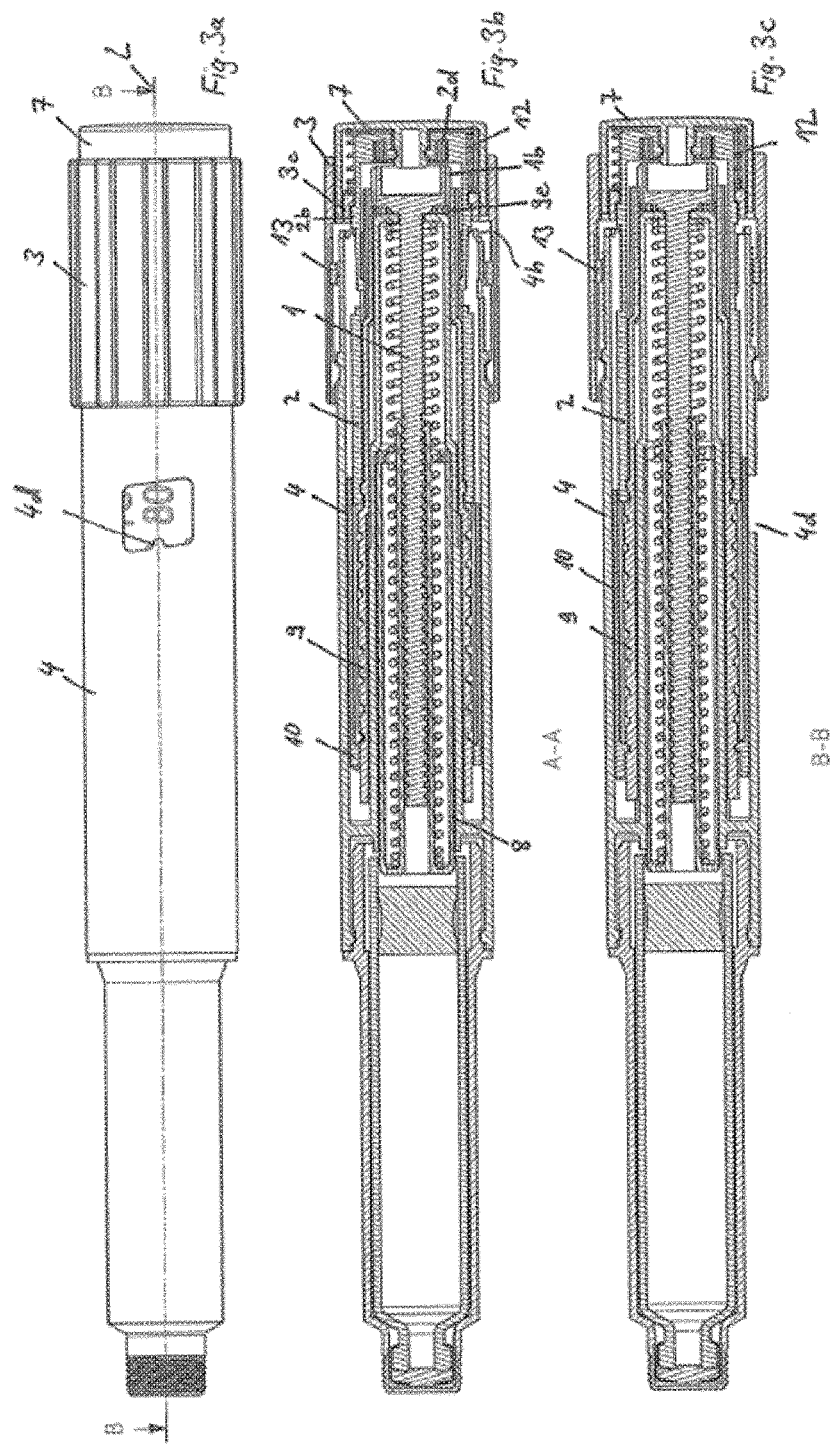
FIGS. 3a-c show the injection device in the views from FIG. 2a in a state in which the maximum adjustable dose has been set.
Figure 4:
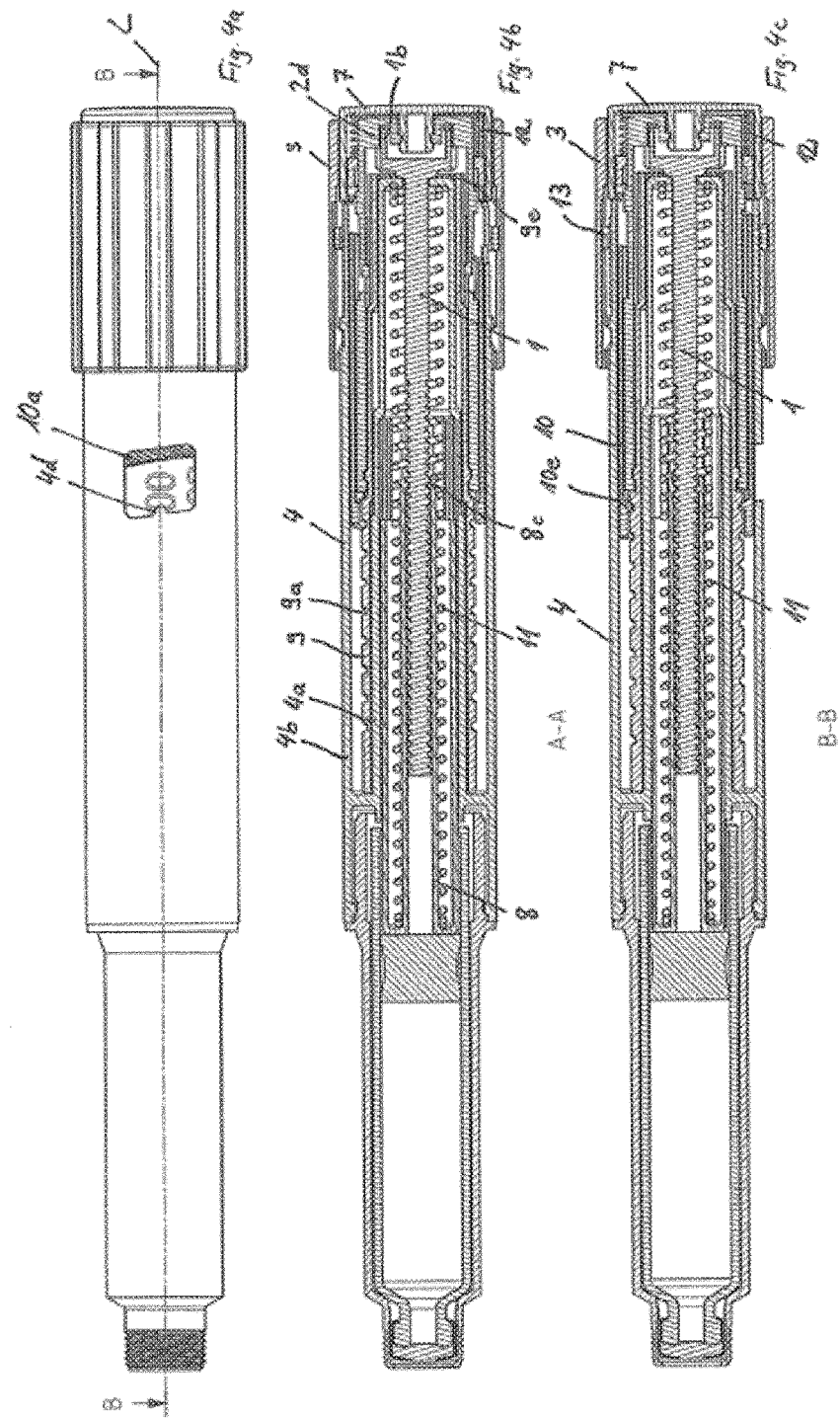
FIGS. 4a-c show the views from FIGS. 2a-c but in a state in which the dose set in FIGS. 3a-c has been completely dispensed and an actuating member is still actuated.
Figure 5:
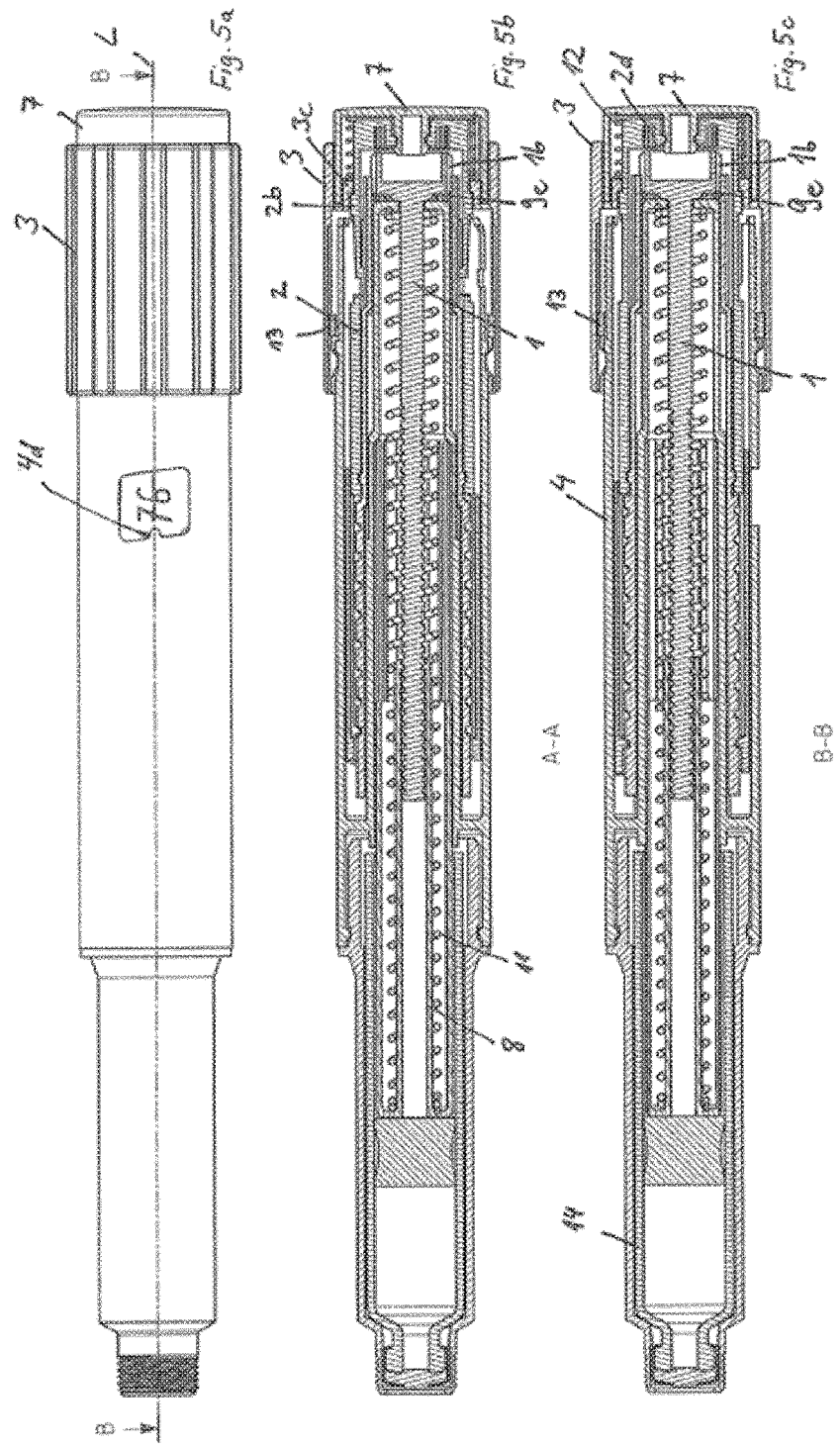
FIGS. 5a-c show the views from FIGS. 2a-c, wherein a driving element of the driving and dosing device has been blocked for a movement to increase the dose, because the dose contained in the product container is smaller than the maximum settable dose.

FIGS. 1-5c illustrate an example of a driving and dosing device that can advantageously be used in connection with embodiments of the invention. This driving and dosing device is known from European Patent Application No. 12 162 777.2.

As can be seen in FIGS. 1 and 2a-2c, for example, a driving and dosing device in which the invention can advantageously be used or integrated has a sleeve-like housing 4 having an outer sleeve 4b that can be gripped by the user with one hand. As can be recognized best from FIG. 2b, the housing 4 further comprises an inner sleeve 4a, which forms an abutment 4i and is arranged concentrically to the outer sleeve 4b. Inner sleeve 4a and outer sleeve 4b are connected to one another via an annular web. Between the outer sleeve 4b and the inner sleeve 4a, an annular gap is formed, in which are arranged a dose indicating element 10, which is formed in particular as a dose indicating drum, i.e., in a sleeve shape, a bearing element 9 and a clutch element 2, which is sleeve-shaped and can also be referred to more particularly as an indicator clutch.

At the distal end of the housing 4, a sleeve-shaped product container receptacle 5 made from a preferably transparent material is arranged, in which a product container 14 in the form of a carpoule is received. The product container 14 is non-detachably connected to the housing 4 by means of the product receptacle 5, so that the driving and dosing device, together with the product container receptacle 5 and the product container 14, forms a disposable injection device, which is disposable as a whole after complete emptying of the product container 14. At its distal end, the product container 14 has a septum 14b, which can be penetrated by a needle that can be positioned at the distal end of the product container 14 or the product container receptacle 5. A piston 14a is arranged in the product container 14, wherein the product to be dispensed is arranged between the septum 14b and the piston 14a. A displacement of the piston 14a in the direction of the septum, or in the distal direction, i.e. the dispensing direction, thus effects dispensing of the product contained in the product container 14. Also shown in FIG. 1 is a protective cap 6, which can be placed over the product container receptacle 5 and is removed before injection of a dose.

The housing 4, particularly the inner sleeve 4a, is engaged with a sleeve-shaped propulsion member 8, which can also be referred to as a plunger. The propulsion member 8 is rotationally fixed relative to the housing 4 and is axially displaceable along the longitudinal axis L (FIG. 2a). Between the inner sleeve 4a and the propulsion member 8, a guide is formed by means of a longitudinal rib 8a and at least one longitudinal guide 4c, which prevents a rotation of the propulsion member 8 relative to the housing 4 and allows an axial movement of the propulsion member 8 relative to the housing 4. The longitudinal rib 8a is preferably formed by an outer sleeve of the propulsion member 8. The propulsion member 8 has an inner sleeve 8b, which in this example has an internal thread 8c at its proximal end that engages with an external thread 1a of a rotary member 1 embodied as a threaded rod. The propulsion member 8 is arranged such that its distal end 8d can act on the piston 14a, in particular can press against the piston 14a.

The housing 4, in particular the proximal end of the inner sleeve 4a, forms an abutment 4i for a dispensing spring 11, which is supported on the abutment 4i and in the area of the distal end of the propulsion member 8. The spring 11 is supported at its distal end on an annular web of the propulsion member 8, which connects the outer sleeve and the inner sleeve of the propulsion member 8. At its proximal end, the spring 11 is supported on the annular web formed by the housing 4 and protruding inward, which forms the abutment 4i.

The dispensing spring 11 is formed as a helical or coil spring, which acts as a compression spring and attempts to push the abutment 4i and the propulsion member 8 apart, i.e., to displace the propulsion member 8 in the distal direction relative to the housing 4. At delivery of the driving and dosing device, i.e., in the initial state thereof, the dispensing spring 11 is sufficiently preloaded that the energy stored in it is sufficient to dispense the product contained in the product container 14 substantially completely, in particular with a number of individual dispensing strokes, between each of which a new dose setting is made. The advantage of such a strongly preloaded spring is that the spring 11 does not have to be cocked during dose-setting, whereby a strength-saving, i.e., simpler dose-setting, is possible for the user of the device.

The threaded engagement between the propulsion member 8 and the rotary member 1 is sufficiently strong that no self-locking of the threaded engagement occurs, i.e., the rotary member 1 is turnable or rotatable relative to the propulsion member 8 about the longitudinal axis L due to the axial force of the dispensing spring 11.

The rotary member 1 is constructed as a threaded rod, which forms the external thread 1a and has an enlarged diameter at its proximal end, more particularly in the shape of a broadened head. Teeth 1b are formed parallel to the longitudinal axis L on the head and act as a second clutch structure, as will be described below. An annular friction surface area with a diameter reduced in comparison to the head is arranged on the head and is in contact with the inward-protruding annular web of the housing 4, which constitutes the abutment 4i. Due to the reduced diameter of the annular friction surface, the point of attack of the resulting friction is shifted closer to the longitudinal axis L, whereby the frictional moment between the rotary member 1 and the housing 4 is reduced.

By rotating the rotary member 1 relative to the housing 4 and the propulsion member 8, the spring 11 can displace the propulsion member 8 by a dispensing stroke in the distal direction that is proportional to the angle of rotation of the rotary member 1. By selectively blocking and releasing the rotary member 1, which can be accomplished by actuating an actuating member 7 constructed as an actuating knob, the movement of the propulsion member 8 relative to the housing 4, i.e., the dispensing stroke of the propulsion member 8, can be controlled in an advantageous manner.

The driving and dosing device further comprises a bearing element 9, which can also be referred to as an indicating drum bearing element and is arranged rotationally fixedly relative to the housing 4 but displaceably along the longitudinal axis L. In the example shown, the bearing element 9 fulfills the task of the displacement element described herein. The bearing element 9 is sleeve-shaped and preferably surrounds the inner sleeve 4a of the housing 4, wherein the outer sleeve 4b in particular surrounds the bearing element 9. The bearing element 9 is engaged with the housing 4, more particularly the inner sleeve 4a, which permits a longitudinal movement of the bearing element 9 relative to the housing 4, but prevents a rotary movement. The engagement can be formed by a longitudinal guide 9f between the bearing element 9 and the inner sleeve 4a.

The bearing element 9 has a thread 9a, in particular an external thread with which a thread 10e, more particularity an internal thread, of the dose indicating element 10 engages. The dose indicating element 10 is screwable relative to the bearing element 9 due to this threaded engagement.

The first embodiment further comprises a signal generation mechanism 2e, 9b that generates an acoustic and/or tactile signal during dose-setting and product dispensing. The signal generation mechanism 2e, 9b is arranged between the clutch element 2 and the bearing element 9 and comprises in particular a catch element 2e and a toothing 9b. The bearing element 9 has a toothing 9b extending over the periphery, in particular the outer periphery. The clutch element 2 has the resiliently arranged catch element 2e engaging with the toothing 9b.

At the proximal end of the bearing element 9, the bearing element has the toothing 9b extending over its circumference, the teeth of which are used, for example, for setting discrete dose-proportional angular steps and/or for producing a slight resistance during dose-setting and/or for generating an acoustic and/or tactile signal, e.g., an audible and tangible click, during dose-setting and product dispensing. Two catch elements 2e, which are resiliently arranged on catch arms and are formed by the clutch element 2, engage with the toothing 9b. The clutch element 2 is connected axially fixedly to the bearing element 9 and rotatably relative to the bearing element 9. For this purpose, the clutch element 2 engages by means of an annular groove 2c with a protrusion 9d extending across the periphery of the bearing element 9. A rotation of the sleeve-shaped clutch element 2 relative to the bearing element 9 causes the catch elements 2e to snap over the toothing 9b and produce the acoustic and/or tactile signal.

The dose indicating element 10 is rotationally fixedly but axially displaceably connected to the clutch element 2, more particularly engaged therewith. This engagement comprises a longitudinal guide 2a, which causes the dose indicating element 10 to be rotationally fixed relative to the clutch element 2, but axially displaceable. Because of the rotationally fixed connection between clutch element 2 and dose indicating element 10, a rotation of the clutch element 2 relative to the bearing element 9 causes the dose indicating element 10 to likewise be rotated and, due to the threaded engagement with the thread 9a, to be screwed along the bearing element 9, in particular, in addition to producing the clicking sounds produced by the catch elements 2e.

The dose indicating element 10 has a dose scale 10b, comprising a plurality of successively arranged scale values, that extends helically, corresponding to the pitch of the thread 10e, over the outer periphery of the dose indicating element. In the example shown, a maximum dose of 80 IU can be set, the scale extending from 0 to 80 with dose values indicated in increments of two.

Likewise corresponding to the pitch of the thread 10e, a mark 10a is arranged in a helical shape over the outer periphery of the dose indicating element 10. This mark 10a is used, as will be described below, to indicate whether the device is actuated or not actuated. The mark 10a is an optional device. It can extend along the entire dose scale 10b or only parts or only a single scale value. In particular, it is only visible toward the end of product dispensing or in the zero position when the driving and dosing device is actuated.

At its proximal end, for example, the dose indicating element 10 has a stop surface 10c pointing and acting in the circumferential direction, which is referred to as the zero dose stop. At the distal end, opposite the proximal end, the dose indicating element 10 has a stop surface 10d pointing and acting in the circumferential direction, which is referred to as the maximum dose stop.

The dose indicating element 10 can be screwed back and forth on the bearing element 9 between the zero dose position and the maximum dose position. In the zero dose position, the zero dose stop 10c, in cooperation with a zero dose mating stop 4f formed by the housing 4, prevents rotation of the dose indicating element 10 in a first rotational direction, namely a rotational direction that would cause a dose less than zero to be set. In this zero dose position, the dose indicating element 10 is rotatable in the opposite, i.e. second, rotational direction.

In the maximum dose position, shown in FIG. 3a, for example, the maximum dose stop 10d, in cooperation with the maximum dose mating stop 9c, which is formed by the bearing element 9, prevents rotation of the dose indicating element 10 in the second rotational direction, which would cause an increase of the dose over the maximum settable value. Rotation in the first rotational direction is possible in the maximum dose position. Although the maximum dose mating stop 9c is formed by the bearing element 9, the maximum dose mating stop 9c can optionally be formed, differing from the present example, by the housing 4. Differing from the example shown, the zero dose mating stop can be formed by the bearing element 9, for example.

The housing 4 has a viewing device 4d in the form of a window, which provides a view of the scale 10b of the dose indicating element 10. A dosing element 3 in the form of a dosing knob is mounted rotatably but axially fixedly on the housing 4. For this purpose, the housing 4 has an annular groove 4g with which an annular shoulder of the dosing element 3 engages. The dosing element 3 has a gripping structure 3b across its periphery, which makes it easier for the user of the device to rotate the dosing element 3 relative to the housing 4. In the non-actuated state of the device, a rotation of the dosing element 3 causes a rotation or helical movement of the dose indicating element 10, whereby the desired dose can be set and read out in the viewing device 4d.

An actuating member 7 in the form of an actuating knob is arranged on the dosing element 3 and is movable relative to the dosing element 3, in particular along the longitudinal axis L, for actuating the device for product dispensing. The actuating member 7 forms the proximal end of the device and can be actuated, in particular displaced relative to the housing 4 and/or the dosing element 3, in an easy manner by the thumb of the hand holding the housing 4. The clutch element 2 is rotatable relative to the actuating member 7, particularly when the dosing clutch 2b, 3c is released, and is axially fixed. The actuating member 7 is preferably snapped together with the clutch element 2 axially fixedly but rotatably.

The driving and dosing device additionally has a reset or clutch spring 12, which is cocked during actuation, more particularly pressing, of the actuating member 7, and which returns the bearing element 9 and/or the actuating member 7 into the non-actuated position when the actuating member 7 is not actuated. Actuating the actuating member 7 causes, in addition to the axial displacement thereof, the axial displacement of the bearing element 9 along the longitudinal axis L. The spring 12 is preferably supported at its distal end on the dosing element 3, and at its proximal end on the actuating member 7. The spring 12 is preferably a helical spring or a coil spring, for example, acting as a compression spring.

The dosing element 3 is rotationally fixed relative to the actuating member 7. The actuating member 7 reaches through an inward-pointing shoulder of the dosing element 3. At the distal end of the preferably pot-shaped actuating member 7, a plurality of teeth are formed, which together form a toothing 7a that, due to the actuation of the actuating member 7, comes into engagement with a toothing 4h formed on the housing 4, particularly at the proximal end of the housing 4, whereby the dosing element 3 is rotationally fixed in relation to the housing 4. The result of this is that setting a dose, i.e. a rotation of the dosing element 3 relative to the housing 4, is not possible if the device is actuated, but instead is only possible if the actuating member 7 is not actuated.

The dosing element 3 forms a clutch structure 3c, more particularly at the inward-protruding shoulder. The clutch structure 3c interacts with a clutch structure 2b on the outer periphery of the clutch element 2 when the actuating member 7 is not actuated. In the non-actuated state of the actuating member 7, the dosing element 3 and the clutch element 2 are rotationally fixed relative to one another due to this clutch engagement. The clutch between the dosing element 3 and the clutch element 2 can also be referred to as a dosing clutch 2b, 3c, which is engaged during dose-setting, i.e. when the actuating member 7 is not actuated, and is disengaged during dose dispensing, i.e. when the actuating member 7 is actuated, the clutch transferring torque in the engaged state and not transferring torque in the disengaged state. The dosing clutch 2b, 3c is disengaged or opened by a displacement of the clutch element 2 relative to the housing 4, more particularly by actuation of the actuating member 7.

The proximal end of the bearing element 9 has a first clutch structure 9e on the inner periphery, which clutch structure is formed by claws or teeth arranged across the periphery that engage with the teeth or claws of the rotary member 1 forming the second clutch structure 1b, more particularly when the actuating member 7 is not actuated. The rotary member 1 is rotationally fixed in relation to the housing 4 by means of this clutch engagement. On the inner periphery of the clutch element 2, there is additionally a third clutch structure 2d, which has a plurality of teeth or claws distributed across the periphery. The third clutch structure 2d is arranged such that, when the actuating member 7 is actuated, the clutch structure comes into a rotationally fixed engagement with the rotary member 1, in particular with the second clutch structure 1b or, alternatively, a fourth clutch structure separate from the second clutch structure 1b that is not shown in this example.

While the actuating member 7 is being pushed for actuation along the longitudinal axis L relative to the dosing element 3, the third clutch structure 2d initially comes into engagement with the second clutch structure 1b. By further displacement of the actuating member 7 relative to the dosing element 3, the first clutch structure 9e disengages from the second clutch structure 1b. Before, during or simultaneously with the release of the engagement between the first clutch structure 9e and the second clutch structure 1b, the clutch structure 2b disengages from the clutch structure 3c and/or the toothing 7a engages with the teeth 4h.

Particularly due to the fact that the first clutch structure 9e is released from the second clutch structure 1b, the dispensing spring 11 can relax, the rotary member 1 being rotated relative to the housing 4; due to the engagement of the second clutch structure 1b with the third clutch structure 2d, the clutch element 2 and thus also the dose indicating element 10 are rotated relative to the housing 4; thereby the dose indicating element 10 is screwed back into its zero dose position and the propulsion member 8 is displaced, proportionally to the circumferential distance between the zero dose stop 10c and the zero dose mating stop 4f, by a dispensing stroke in the distal direction relative to the housing 4. The rotation of the clutch element 2 relative to the bearing element 9 causes the catch elements 2e to snap over the toothing 9b, more particularly in dose-proportional angular steps, and produce the acoustic and/or tactile signal.

The driving and dosing device has a dose limiter 13, in the form of a ring, a ring segment or a nut, having a thread 13b on its inner periphery that engages with a thread 4e arranged on the outer periphery of the housing 4, so that the limiter 13 can be screwed relative to the housing 4. At the outer periphery, the limiter 13 has an engagement member 13a, which engages in a longitudinal guide 3a on the inner periphery of the dosing element 3, so that the dose limiter 13 is rotationally fixed but axially displaceable relative to the dosing element 3. A stop projection, from which the limiter 13 has a distance proportional to the maximum product quantity that can be dispensed from the product container 14, is formed on the dosing element 3 or the housing 4. Since the dosing element 3 rotates relative to the housing 4 during dose-setting and is not rotated during dose dispensing, the limiter 13 can form a counting mechanism, which adds the already dispensed individual doses and the currently set dose and correspondingly moves the housing 4 closer and closer to the stop projection of the dosing element 3. A dose increase causes the limiter 13 to be moved toward the stop projection. A dose reduction causes the limiter 13 to be moved away from the stop projection. If the remaining dose indicated in the product container 14 is less than the maximum dose that can be set with the driving and dosing device, the limiter 13 comes into contact with the stop projection, so that a rotation of the dosing element 3 relative to the housing 4 in a rotational direction that would result in an increase of the dose is blocked.

The clutch formed from the first, second and third clutch structures 9e, 1b, 2d as well as optionally the fourth clutch structure can also be referred to as a dispensing clutch due to its interaction.

FIGS. 2a-2c show the driving and dosing device, which can also be referred to as an injection device, in the initial or delivery state, more particularly the state before first use. The product dose indicated in the viewing device 4d is 0. Actuation of the actuating member 7 would result in no dose being dispensed. The limiter 13 is a distance away from the stop projection that is proportional to the quantity of product contained or injectable in the product container 14, e.g. 300 IU.

To set the product dose, the dose setting member 3 is rotated relative to the housing 4, whereby the clutch element 2 and thus also the dose indicating element 10 are rotated relative to the housing 4 due to the clutch engagement 2b, 3c. In the process, the dose indicating element 10 screws along the bearing element 9 due to the thread engagement of the thread 10e with the thread 9a. In particular, the distance between the zero dose stop 10c and the zero dose mating stop 4f is increased proportionally to the dose shown in the viewing device 4d. In addition, an audible and tactile signal is generated during rotation due to the snapping of the catch elements 2e over the toothing 9b.

FIGS. 3a-3c show the driving and dosing device in a state in which a maximum settable dose, 80 IU in this example, has been set, which can be read out in the viewing device 4d. A further increase of the dose is not possible due to the interaction, more particularly the contact, of the maximum dose stop 10d with the maximum dose mating stop 9c. As can best be recognized from FIGS. 3b and 3c, the dose limiter 13 has been advanced or shifted toward the stop projection corresponding to 80 IU.

To dispense the dose shown for the sake of example in FIG. 3a, the actuating member 7 is actuated, more particularly pressed, i.e. displaced in the distal direction relative to the housing 4 and the dosing element 3, whereby the clutch element 2 and the bearing element 9 as well as the dose indicating element 10 are displaced distally relative to the housing 4, more particularly against the force of the coupling or reset spring 12. Because the dose indicating element 10 is displaced axially relative to the housing 4 and the viewing device 4d, the mark 10a shown in FIG. 1 appears in the viewing device 4d (FIG. 4a), whereby the user can read visually that the device has been actuated. The displacement of the dose indicating element 10 relative to the housing 4 and the viewing device 4d moves the mark 10a along the longitudinal axis L from a position in which it is concealed by the housing 4 into a position in which it is shown in the viewing device 14d.

The actuation of the actuating member 7 additionally causes the third clutch structure 2d to engage with the second clutch structure 1b and the first clutch structure 9e to disengage from the second clutch structure 1b, so that the rotary member 1 is no longer rotationally fixed in relation to the housing 4, but is rotatable and is rotationally fixed in relation to the clutch element 2 and the dose indicating element 10. Actuating the actuating member 7 also causes the dosing clutch 2b, 3c to disengage or be opened and the front toothing 7a to engage with the front toothing 4h. In the actuated state of the actuating member 7, the rotary member 1 is rotationally fixed relative to the dose indicating element 10, whereby the rotary member 1 and the dose indicating element 10 can rotate jointly relative to the housing 4. The force on the propulsion member 8 from the energy stored in the dispensing spring 11 causes a rotation of the rotary member 1 and the dose indicating element 10 relative to the housing 4 due to the threaded engagement of the propulsion member 8 with the rotary member 1, whereby the dose indicating element 10 is screwed back on the bearing element 9 in the direction of the zero dose position and the dose indicated in the viewing device 14d is counted down. At the same time, the propulsion member 8 is moved by the dispensing spring 11 in the distal direction relative to the housing 4 by the dispensing stroke, which is proportional to the previously set dose. When the dose indicating element 10 has reached its zero position (FIGS. 4a-4c) the previously set dose or single dose has been dispensed. If the user releases the actuating member 7, still shown pressed down in FIGS. 4a-4c, the coupling or reset spring 12 resets the actuating member 7, the clutch element 2, the bearing element 9 and the dose indicating element 10 into the position shown, for example, in FIG. 2a wherein the mark 10a again disappears under the housing 4 or is concealed by the housing 4. During resetting, the aforementioned elements are displaced in the proximal direction relative to the housing 4 or the dosing element 3.

During resetting of the device by means of the spring 12, the first clutch structure 9e is engaged with the second clutch structure 1b, and the third clutch structure 2d is disengaged from the second clutch structure 1b. The rotary member 1 is now again rotationally fixed in relation to the housing 4, the dosing element 3 again being rotatable together with the dose indicating element 10 relative to the housing 4 and/or the viewing device 4d and/or the rotary member 1 for another setting of a product dose or single dose. In addition, the front toothings 7a and 4h are released from engagement during resetting, and the dosing clutch 2b, 3c is reengaged, whereby the dosing element 3 is rotationally fixed relative to the clutch element 2 and the dose indicating element 10.

FIG. 5a shows the driving and dosing device in the position in which the limiter 13 assumes its stop position, i.e. strikes against the stop projection, whereby the limiter 13 blocks setting to a value that exceeds the residual amount contained in the product container 14. In the example shown, the product container 14 still contains 76 IU, while a maximum of 80 IU could be set with the driving and dosing device. Because the limiter 13 is already in contact with the stop projection at 76 IU, the dosing element 3 is blocked from a rotation in the second direction, which would cause an increase of the dose. Decreasing the dose, however, is possible by turning the dosing element 3 in the first rotational direction.

The dose shown in the viewing device 4d is dispensed by actuating the actuating member 7. Since the product container 14 is then completely empty, the entire driving and dosing device, or injection device, is disposed of. This is therefore a disposable injection device. In principle however, the driving and dosing devices shown herein can also be used in connection with multiple-use injection devices, in which an empty product container 14 is exchanged for a new one.

The driving and dosing device described with reference to FIGS. 1-5c is known from European Patent Application No. 12 162 777.2. In order to ensure that, with the actuating member fully actuated, the rotary member 1 in fact does carry out its rotary movement for dispensing the dose, the actuating member 7 is coupled to the rotary member 1 in such a manner that actuating or pressing the actuating member 7 causes the rotary member 1 to rotate relative to the housing 4 already when the clutch 9e, 1b is still closed. At least the rotary member 1 is thereby already set into rotary movement, so that static friction in the driving and dosing device can be overcome, even if the parts have become "stuck" due to extended storage.

Disclosed Embodiments

Figure 6:
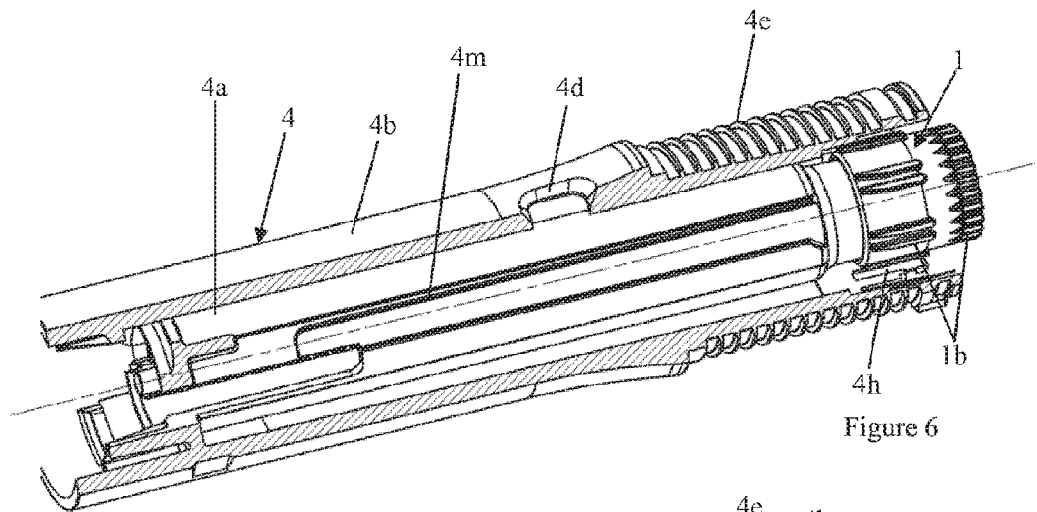
FIGS. 6-9 show various views of a first embodiment of the invention.
Figure 7:
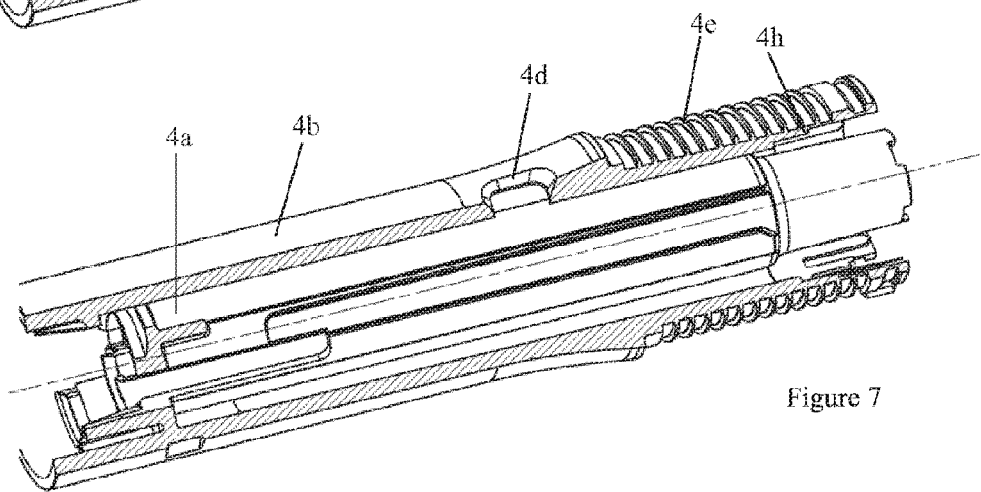
Figure 8:
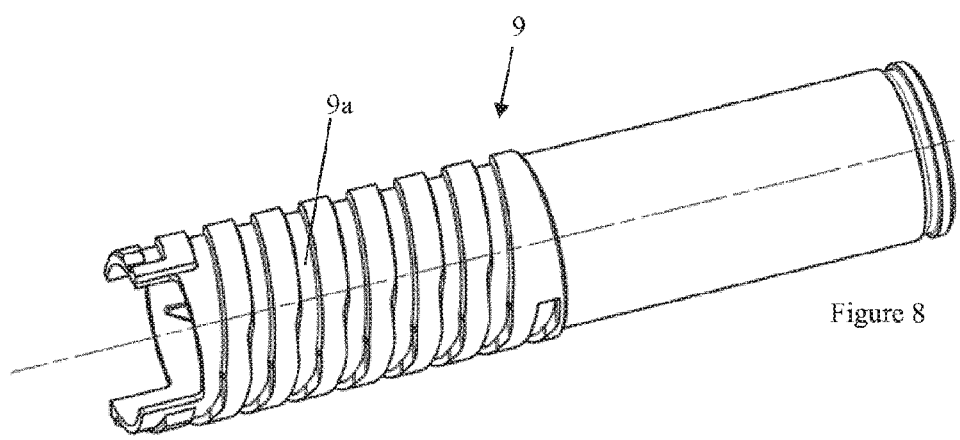
Figure 9:
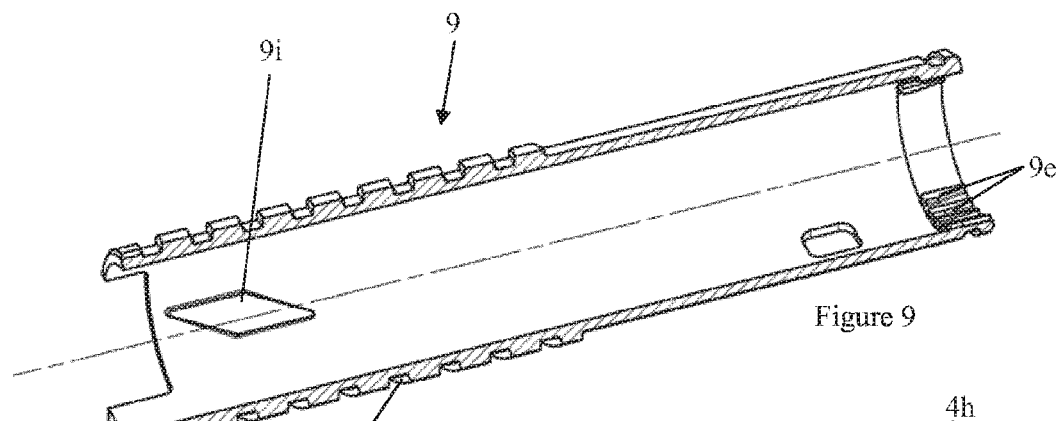
Figure 10:
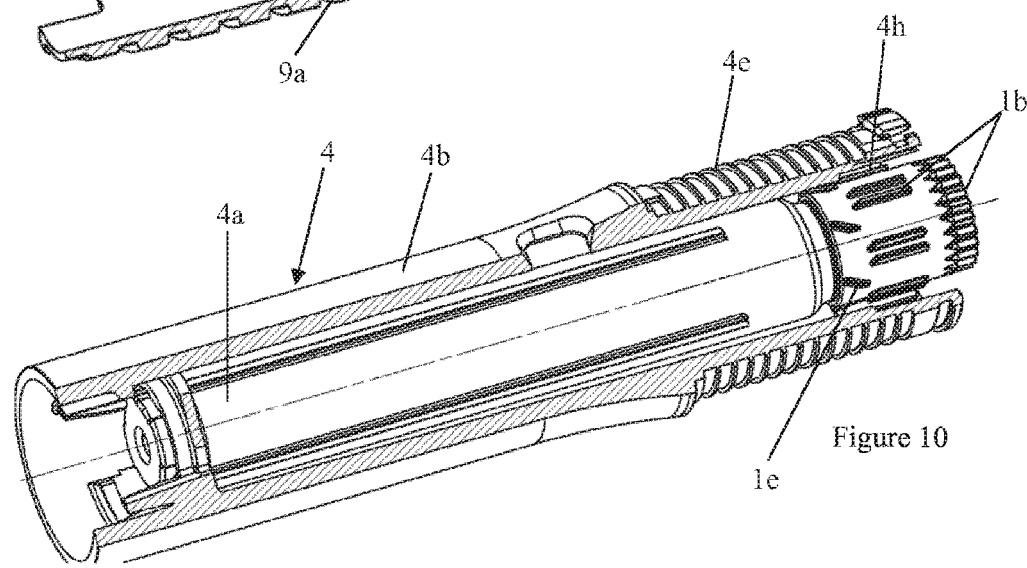
FIGS. 10-14 show various views of a second embodiment of the invention.
Figure 11:
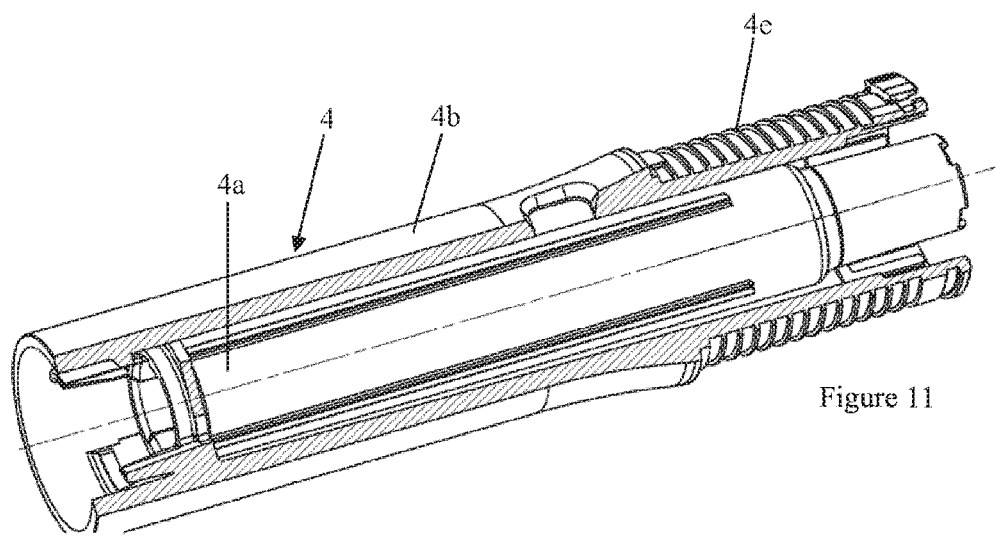
Figure 12:
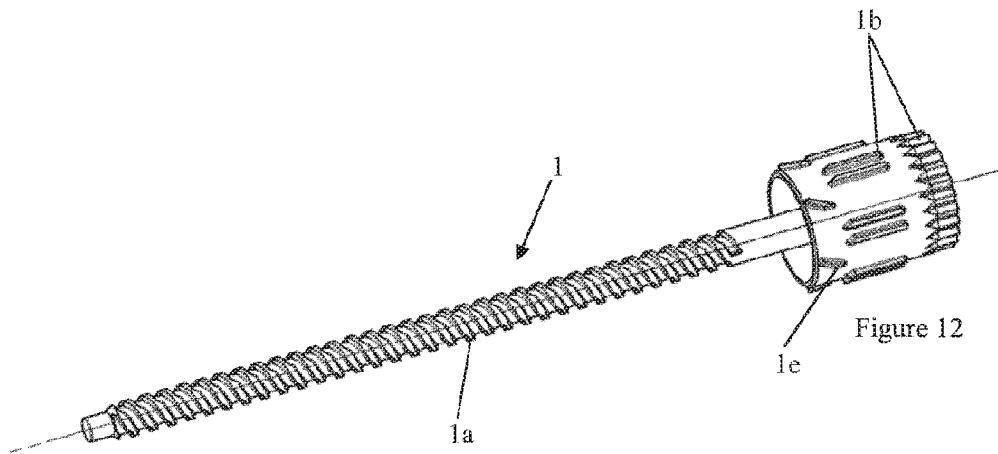
Figure 13:
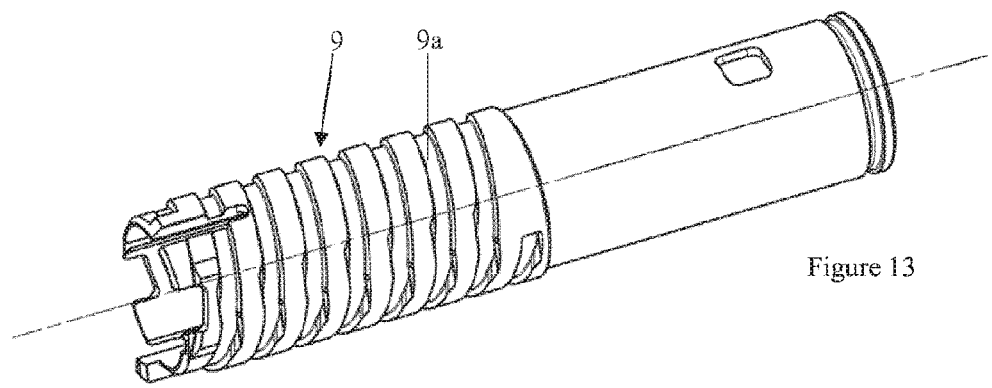

FIGS. 6-9 show various views of a first embodiment of the invention. The features that differ from those of the preceding embodiment will be described below, and therefore the reader is referred to FIGS. 1-5c in other respects. Identical reference numbers designate parts that are at least functionally equivalent. With reference to FIGS. 6 and 7, the inner sleeve 4a includes a guide track 4m, which is shaped in particular in the form of a groove. The elongated guide track 4m, extending along and in particular parallel to the longitudinal axis L, has a proximal guide track section and a distal guide track section, which are connected by a transition section and in particular terminate there, as can best be seen from FIGS. 6 and 7. The proximal guide track section 4m is arranged offset by an angle about the longitudinal axis L relative to the distal guide track section. The groove-like guide track 4m is open at least toward the outside or toward the bearing element 9, wherein a protrusion 9i (FIG. 9) on the inner periphery of the bearing element 9 engages with the guide track 4m. For example, the shape of the protrusion 9i can be adapted to the transition region between the proximal and distal guide track sections in such a manner that if the protrusion 9i is displaced in the distal direction, the protrusion 9i is guided from the proximal guide track section to the distal guide track section, in particular through the transition section, in such a manner that the bearing element 9 undergoes a rotary movement relative to the longitudinal axis L. Since the protrusion 9i is fixedly formed on the bearing element 9 in the example shown, the rotary movement exerted on the protrusion 9i by the displacement thereof is transmitted to the bearing element 9.

The protrusion 9i can be round, for example, more particularly circular, in which case the transition region between the proximal and distal guide track sections can be slanted or thread-shaped (not shown). In the embodiment shown, the protrusion 9i is a rhombic cam 9i. The end of the rhombic cam 9i pointing in the distal direction is displaced during actuation of the actuating member 7 out of the proximal guide track section at least partially into the distal guide track section due to displacement of the bearing element 9, wherein the proximal guide track section and the distal guide track section of the guide track 4m overlap one another in the transition region relative to the angular position about the longitudinal axis L. The inclined face, pointing in the distal direction, that is arranged between the faces parallel to the longitudinal axis L slides on the distal edge that is formed between the proximal and distal guide track section in such a manner that the rhombic cam 9i, and thus the bearing element 9, are set into a rotary movement about the longitudinal axis L in the first rotational direction.

The rhombic cam 9i has two parallel faces facing the circumferential direction and arranged parallel to the longitudinal axis L. These faces are a distance away from one another that corresponds approximately to the width of the guide track 4m, in particular the proximal and/or distal guide track sections. The inclined, mutually parallel faces that face in the distal direction and in the proximal direction, and which connect the faces of the rhombic cam 9i that extend parallel to the longitudinal axis L, can function, for example, as transmission surfaces.

The bearing element 9 has a first clutch structure 9e, which is designed as internal toothing and, when the actuating member 7 is not actuated or is not in its (completely) actuated position, engages torsion-free with the second clutch structure 1b, which is formed as external toothing on the rotary member 1. The first clutch structure 9e and the protrusion 9i are arranged relative to one another such that the bearing element 9 already rotates in the first rotational direction when the clutch 9e, 1b is still closed, whereby the rotary member 1 is also rotated. This happens in an intermediate position of the actuating member 7 between the non-actuated position and the actuated position. If the actuating member 7 is brought from the intermediate position into the actuated position, the clutch 9e, 1b is opened, whereby the rotary member 1 is driven rotationally by the dispensing spring 11.

When the actuating member 7 is released, the spring 12 resets the actuating member 7 into its non-actuated position, wherein the inclined face pointing in the proximal direction of the cam 9i slides on the proximal edge that is formed between the proximal and distal guide track section, so that the cam 9i and thus the bearing element 9 are set into a rotary motion in the second direction about the longitudinal axis L. The clutch 9e, 1b is closed in this case, so that the rotary member 1 is also rotated in the second direction, whereby the propulsion member 8 is moved at least a very small way in the proximal direction. Thereby the piston of the product container 14 is relieved and the spring 11 is at least minimally tensioned.

Figure 14:
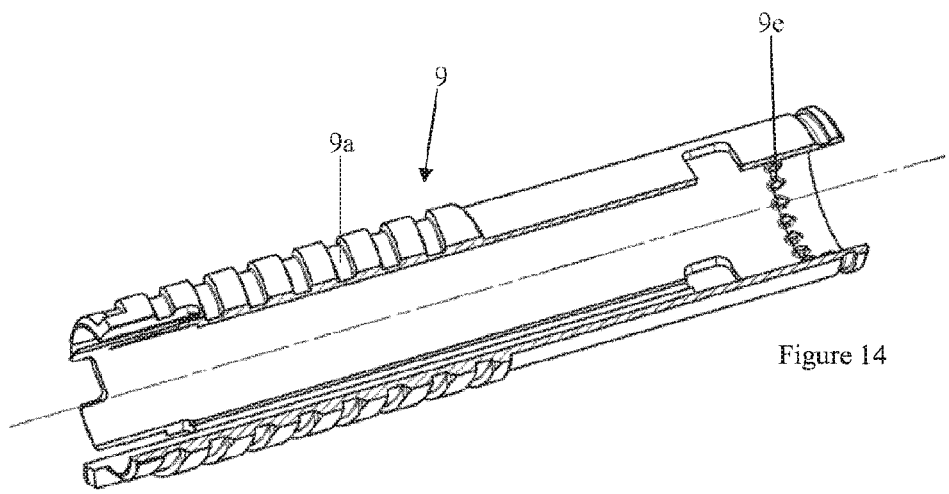
Figure 15:
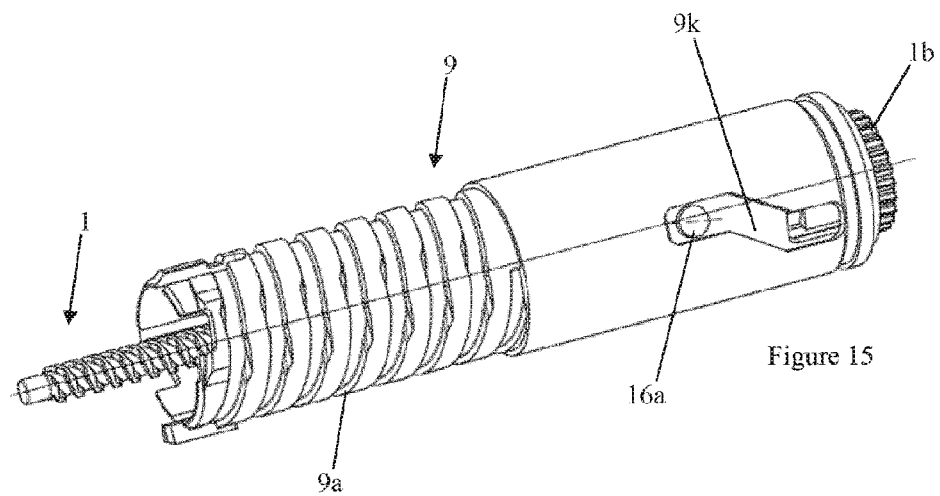
Figure 16:
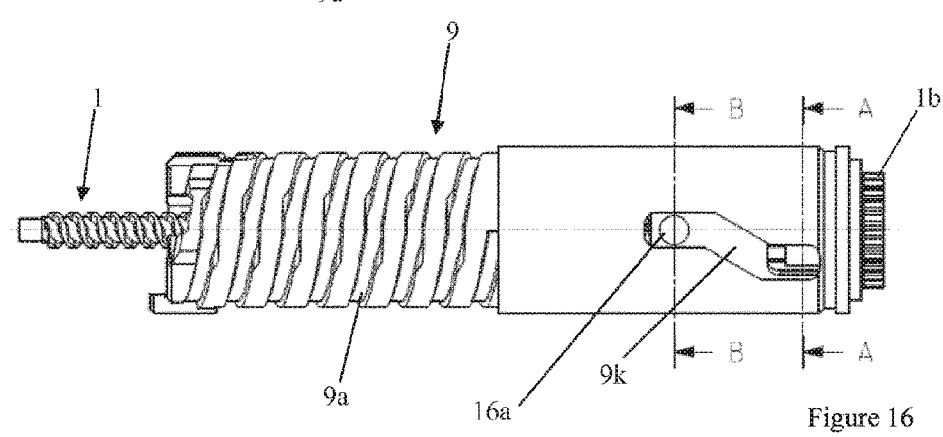
Figure 17:
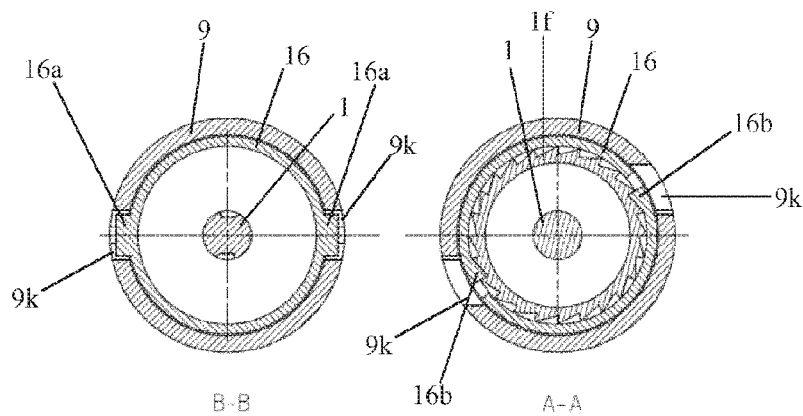

The second embodiment, from FIGS. 10-14, comprises a first clutch structure 9e designed as internal toothing on the interior periphery of the bearing element 9 (FIG. 14). The bearing element 9 is rotationally fixed and axially displaceable relative to the housing 4, the internal sleeve 4a having webs extending parallel to the longitudinal axis L that engage with corresponding recesses or grooves on the interior periphery of the bearing element 9 (FIG. 14). As described, the rotary member 1 has a second clutch structure 1b, which is designed as external toothing. The rotary member 1 further comprises at least one, preferably a plurality of transmission surfaces 1e, which are arranged at an angle relative to the longitudinal axis L and on which the first clutch structure 9e slides during actuation of the actuating member 7 or during displacement of the bearing element 9 in the distal direction relative to the housing 4, whereby the rotary member 1 is set into a rotary movement when the actuating member 7 is displaced from its initial position to the actuated position. The first clutch structure 9e of the bearing element 9 disengages from the second clutch structure 1b and moves into engagement with the transmission surface 1e. The at least one transmission surface 1e is formed by at least one protrusion, which preferably points radially outward. The protrusion 1e can be rib-shaped and is preferably arranged distal to the second clutch structure 1b.

The second clutch structure 1b, the first clutch structure 9e and the at least one transmission surface 1e can be matched to one another in such a manner that the first clutch structure 9e is still engaged with the second clutch structure 1b when the first clutch structure 9e slides on the transmission surface 1e, or disengages from the second clutch structure 1b when the clutch structure 9e is sliding on the at least one transmission surface 1e.

In the third embodiment, shown in FIGS. 15-23, an intermediate sleeve 16 is arranged, in particular geometrically and/or kinematically, between the rotary member 1 and the bearing element 9. The immediate sleeve 16 has a resiliently arranged latching cam 16b, which engages resiliently with external toothing of the rotary member 1, the external toothing having a plurality of sawtooth-shaped teeth arranged over the periphery of the rotary member 1. The external toothing is formed on the external periphery of the rotary member 1. The sawtooth-like shape of the external toothing has the effect that, during rotation of the intermediate sleeve 16 in the first rotational direction, which effects a dispensing of the product, the rotary member 1 is driven, and that the rotary member 1 can be rotated relative to the immediate sleeve 16 in the first direction, which effects the dispensing of the product.

The intermediate sleeve 16 has a guide cam 16a, which is formed on the outer periphery of the intermediate sleeve 16 and protrudes radially outward, i.e. away from the longitudinal axis L. The guide cam 16a engages with a groove-like guide track 9k, which is formed by the sleeve-like bearing element 9. The guide track 9k is open at least toward the inner circumference or toward the intermediate sleeve 16. The guide track 9k has a proximal guide track section and a distal guide track section that are connected to one another via an intermediate section, which is arranged inclined relative to the distal and proximal guide track sections. The proximal and distal guide track sections are parallel to the longitudinal axis L and angularly offset relative to one another about the longitudinal axis L.

Figure 18:
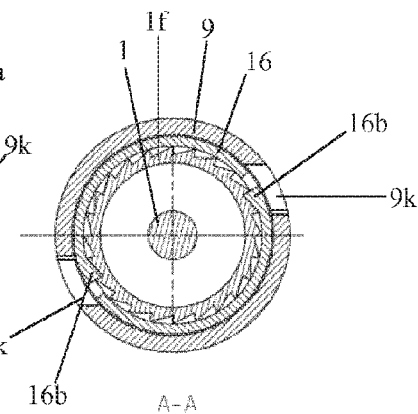

In the non-actuated position of the actuating member 7, the guide cam 16a is arranged in the distal guide track section of the guide track 9k. When the actuating member 7 is pressed into the actuating position, the bearing element 9, which is connected rotationally fixedly and axially displaceably to the housing 4, is displaced in the distal direction relative to the guide cam 16a or to the intermediate sleeve 16, and in particular relative to the housing 4, whereby the guide cam 16a comes into engagement with the intermediate section of the guide track 9k, so that the guide cam 16a and the intermediate sleeve 16 are rotated in the first rotational direction, whereby the rotary member 1 is driven in the first rotational direction by the intermediate sleeve 16. The latching cam 16b is held in the toothing 1f, more particularly by the inner periphery of the bearing element 9. When the actuating member 7 is in its actuation position, the proximal guide track section of the guide track 9k is radially above the latching cam 16b, so that the latching cam 16b can be elastically moved radially outward (FIG. 18). By means of the drive spring 11 and the closed clutch 1b, 2d, the rotary member 1 is rotated in the first rotational direction relative to the intermediate sleeve 16, so that the propulsion member 8 is moved in the distal direction. During the rotation of the rotary member 1 relative to the intermediate sleeve 16, the toothing if catches on the latching cam 16b, so that the latching cam 16b is pressed resiliently out of and into engagement with the toothing 1f.

In the embodiments in which the latching cam 16b is held in engagement with the toothing if by the inner periphery of the bearing element 9 when the actuating member 7 is not in its actuated position, the toothing if need not necessarily be equipped with sawtooth-shaped teeth, but can be equipped with teeth of any type, since the engagement of the latching cam 16b with the toothing if during rotation of the intermediate sleeve 16 in the first rotational direction is effected in that the interior periphery of the bearing element 9 holds the latching cam 16b in engagement with the toothing 1f, so that this engagement is not detachable so long as the actuating member 7 is not in its actuation position.

In the first through third embodiments, the bearing element 9 can alternatively be referred to as a displacement element 9, since it performs the task of the displacement element described herein.

Figure 24:
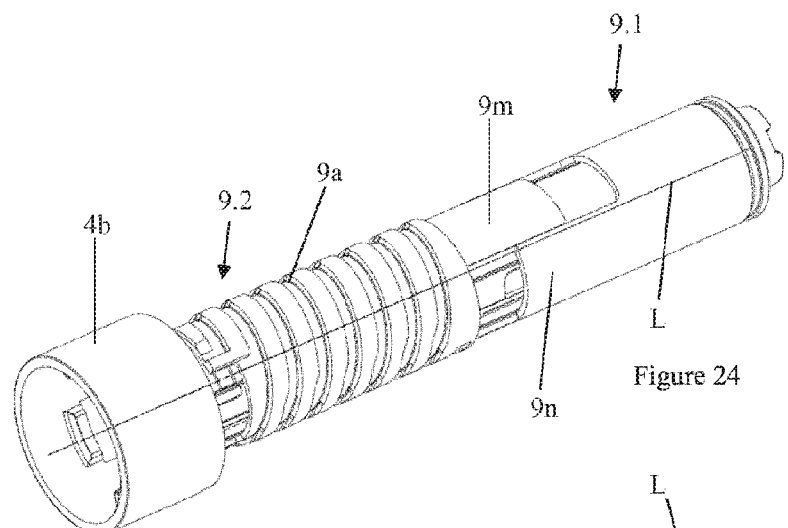
FIGS. 24-26 show various views of a housing section and multi-part bearing element of a fourth embodiment of the invention.
Figure 25:
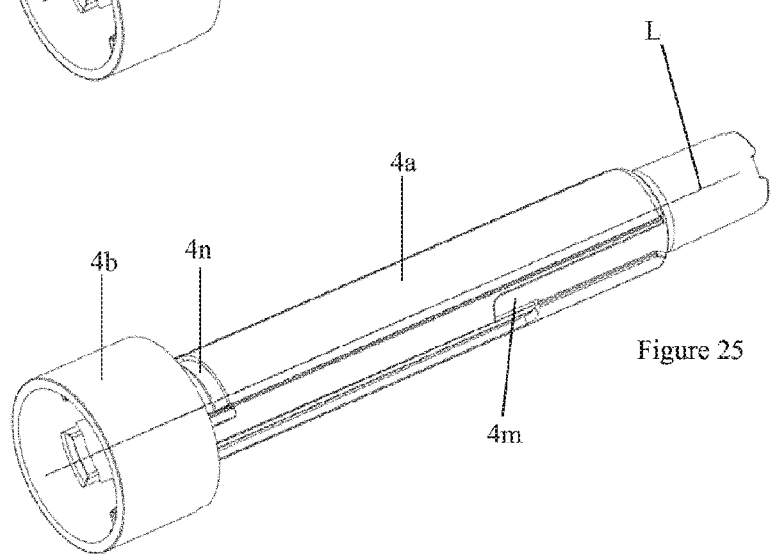
Figure 26:
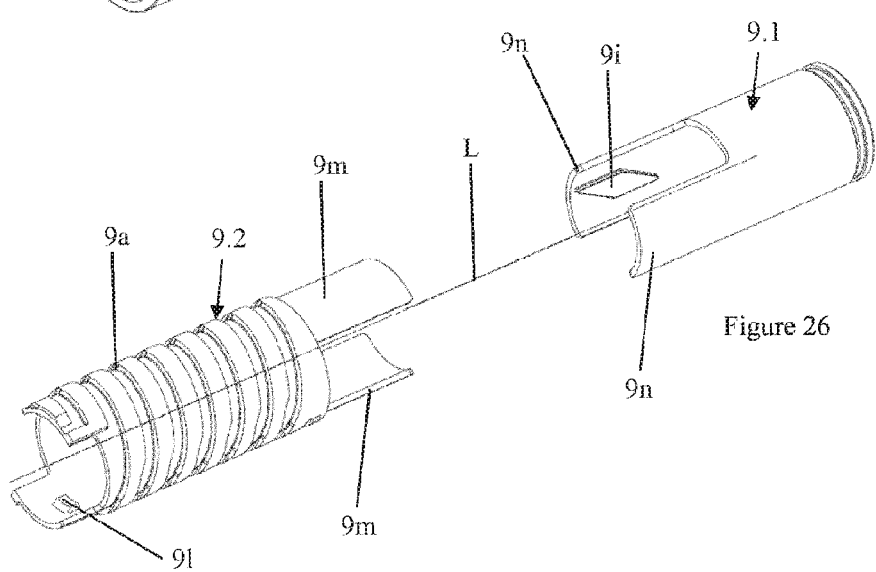

The fourth embodiment, which is shown in FIGS. 24-26, solves the problem of preventing a displacement of the dose indicating drum 10 along the longitudinal axis L relative to the viewing device 4d and/or the housing 4 during the displacement of the actuating member 7. For some users or applications, it can be advantageous if the display of the dose is not influenced by pressing the actuating member 7 as long as the actuating member 7 has not yet reached its actuating position. The basic embodiment shown in FIGS. 1-5c can be modified for this task by means of the embodiments shown in FIGS. 24 and 26. Only the parts which are required for understanding the modification, and in particular those which are modified, are shown in FIGS. 24-26.

FIGS. 24 and 25 show a portion of the outer sleeve 4b, which is connected to the inner sleeve 4a via radial webs (not visible because they are concealed by the portion of the outer sleeve 4b). The inner sleeve 4a has a groove-like guide track 4m, analogously to the embodiment from FIGS. 6-9. The reader is referred to the description for FIGS. 6-9 for the design of the guide track 4m. It should also be pointed out that the transition region between the proximal guide track section and the distal guide track section in FIGS. 24-26 is displaced somewhat in the proximal direction, since the protrusion 9i is likewise arranged farther in the proximal direction than in the embodiment from FIGS. 6-9.

The bearing element 9 in this embodiment comprises two parts, namely a first bearing element part 9.1 and a second bearing element part 9.2. In particular, the bearing element part 9.1 performs the task of the displacement element described herein and can optionally be referred to as a displacement element.

The second bearing element part 9.2 has the external thread 9a, with which the internal thread of the dose indicating element 10 is engaged, so that the dose indicating element 10 can be screwed along the external thread 9a. The second bearing element 9.2 and the housing, particularly the internal sleeve 4a, engage in such a manner that the bearing element part 9.2 is rotatable relative to the housing 4 and about the longitudinal axis L, and is non-displaceable along the longitudinal axis L. The second bearing element part 9.2 is sleeve-shaped and can therefore be referred to as the second bearing element sleeve.

The first bearing element part 9.1 is likewise sleeve-shaped and can therefore be referred to as the first bearing element sleeve 9.1. The first bearing element part 9.1 is axially fixedly connected to the actuating member 7 (see FIG. 2b, for example), so that the first bearing element part 9.1 moves along with the actuating member 7 during actuation of the actuating member in the distal direction relative to the housing 4, and moves in the proximal direction relative to the housing 4 when the actuating member 7 is released.

The first bearing element 9.1 has, similarly to the displacement element 9 from FIGS. 6-9, an inward-directed protrusion 9i, designed as a rhombic cam, on the inner periphery. The protrusion 9i engages with the guide track 4m, namely the proximal guide track section, when the actuating member 7 is non-actuated. If the actuating member 7 is actuated, i.e., displaced by the actuation stroke in the distal direction along the longitudinal axis L, the protrusion 9i is also displaced into the transition region. The operation corresponds to that from FIGS. 6-9, so the reader is referred to the corresponding description. Due to the sliding of the inclined face of the protrusion 9i on the distal edge of the transition section, the first bearing element part 9.1 is rotated about the longitudinal axis L, namely in the first rotational direction. When the actuating member 7 is released, the protrusion 9i moves in the proximal direction, wherein the inclined face pointing in the proximal direction slides along the other proximal edge of the transition region, so that the first bearing element part 9.1 is rotated in the second rotational direction.

The first bearing element part 9.1 further comprises the first clutch structure 9e in the form of internal toothing (not visible). For the design of the first clutch structure 9e, the reader is analogously referred to the description for or on FIG. 9.

The first clutch structure 9e engages rotationally fixedly with the second clutch structure 1b when the actuating member 7 is non-actuated or not completely actuated. During the performance of the actuating stroke of the actuating member 7, the first bearing element part 9.1 is rotated already when the clutch 9e, 1b is still closed. This has the effect that the rotary member 1 is rotated along with the first bearing element part 9.1. The operation corresponds to that from FIGS. 6-9, and therefore the reader is referred additionally to the corresponding parts of the description.

The first bearing element part 9.1 and the second bearing element part 9.2 are engaged with one another axially displaceably and rotationally fixedly. Therefore the second bearing element part 9.2 moves along with the rotation of the first bearing element part 9.1. The second bearing element part 9.2, however, is decoupled from the axial movement of the first bearing element part 9.1. This has the effect that the second bearing element part 9.2 is not displaced along the longitudinal axis L, whereby the dose indicating element 10—apart from the return rotation during the dispensing of the product—is not displaced along the longitudinal axis L relative to the viewing device 4d of the housing 4.

In the example shown, the first bearing element 9.1 has two legs 9n directed in the distal direction, between which the two legs 9m that are formed by the second bearing element part 9.2 and by the proximal end thereof protrude. The legs 9m, 9n mutually guide one another and thereby prevent the first bearing element part 9.1 from being rotatable relative to the second bearing element part 9.2, but at the same time allow the first bearing element part 9.1 to be displaceable relative to the second bearing element part 9.2 along the longitudinal axis L.

For the axially fixed and rotatable connection between the second bearing element part 9.2 and the inner sleeve 4a, a groove 4n running in the circumferential direction, with which an engagement element 9*l*, in particular a protrusion on the inner periphery of the second bearing element part 9.2, is arranged on the inner sleeve 4*a*.

The clutch element 2 (FIGS. 1-5*c*) engages axially fixedly and rotatably with the first bearing element part 9.1, for which the first bearing element part 9.1 has an annular circumferential collar at the proximal end.

The clutch 1*b*, 9*e*, the clutch 1*b*, 2*d*, the cam 9*i* and the transition region are matched to one another and in particular positioned relative to one another such that during the displacement of the actuating member 7 from the non-actuated position into the actuated position, first the clutch 2*d*, 1*b* is closed, thereafter the bearing element part 9.1 is rotated by means of the cam 9*i*, and only after the start of the rotation of the bearing element part 9.1 is the clutch 1*b*, 9*e* opened.

During rotation of the bearing element part 9.1, particularly due to the closed clutch 1*b*, 2*d*, the dose indicating drum 10 carries out a rotation, more particularly without a movement along the longitudinal axis L, relative to the viewing device 4*d* and/or the housing 4. During this time, there is no rotary movement and therefore also no screwing movement between the bearing element part 9.2 and the dose indicating drum 10.

What is claimed is:

1. A driving and dosing device for an injection device for administering a liquid product, comprising:
   a housing comprising an abutment;
   an actuating member displaceable relative to the housing to initiate a product dispensing;
   a propulsion member movable relative to the abutment in a dispensing direction in order to effect the product dispensing;
   a spring operable between the propulsion member and the abutment, wherein before a first use of the driving and dosing device, the spring is preloaded upon delivery of the device with a sufficient energy to dispense a maximum dispensable product quantity from a product container within the injection device;
   a rotary member rotatable relative to the housing to cause the spring to move the propulsion member in the dispensing direction; and
   a clutch, wherein the clutch is opened upon actuating the actuating member such that the clutch releases the rotary member to cause rotation of the rotary member relative to the housing in a first rotational direction, and
   wherein the actuating member is coupled to the rotary member such that during actuation of the actuating member, the rotary member is caused to rotate relative to the housing while the clutch is in a closed position.

2. The device of claim 1, wherein prior to an actuation of the actuating member, the clutch is in the closed position, and during actuation of the actuating member when the clutch is in the closed position, rotation of the rotary member relative to the housing is less than 45°.

3. The device of claim 1, wherein prior to an actuation of the actuating member, the clutch is in the closed position, and during actuation of the actuating member when the clutch is in the closed position, rotation of the rotary member relative to the housing is in the first rotational direction.

4. The device of claim 1, wherein the actuating member is coupled to the rotary member such that a release of the actuated actuating member causes the rotary member to rotate relative to the housing in a second rotational direction opposite from the first rotational direction.

5. The device of claim 1, wherein the propulsion member moves in the dispensing direction to displace a piston of the product container during rotation of the rotary member in the first rotational direction, and during movement of the actuating member from an actuated position to a non-actuated position, the propulsion member moves opposite the dispensing direction such that the piston is relieved of pressure therefrom.

6. The device of claim 1, further comprising a first part forming a first transmission element and a second part forming a second transmission element, wherein the first transmission element and the second transmission element slide along one another during actuation of the actuating member.

7. The device of claim 6, wherein the first part comprises the housing or an element fixed thereto, and the second part comprises a portion of the clutch configured as a bearing element and is axially displaceable relative to housing.

8. The device of claim 6, wherein the first part comprises the rotary member and defines a portion of the clutch, and the second part comprises a bearing element and defines another portion of the clutch which is rotationally fixed and axially displaceable in relation to the housing.

9. The device of claim 1, wherein the rotary member comprises a plurality of teeth resiliently engaged with a latching cam, the latching cam formed by a sleeve surrounding the rotary member.

10. The device of claim 9, wherein the sleeve forms a first portion of the clutch, and a bearing element forms a second portion of the clutch, the bearing element being rotationally fixed and axially displaceable in relation to the housing.

11. The device of claim 10, wherein the bearing element surrounds at least a portion of the sleeve.

12. The device of claim 1, further comprising a dosing element configured to rotate relative to the housing to set a dose, wherein actuating the actuating member causes the propulsion member to move in the dispensing direction by a dispensing stroke to dispense the set dose.

13. The device of claim 1, wherein in response to releasing the actuated actuating member, the clutch blocks rotation of the rotary member relative to the housing.

14. The device of claim 1, wherein the spring is configured as a torsion spring and is supported on the rotary member and the abutment.

15. The device of claim 14, wherein the propulsion member is guided by the housing.

16. The device of claim 15, wherein the spring drives the propulsion member and the propulsion member drives the rotary member.

17. The device of claim 1, wherein one of rotary member and the propulsion member is configured as a threaded rod and the other of the rotary member and the propulsion member is configured as a threaded nut, and wherein the threaded nut is engaged with the threaded rod.

18. The device of claim 1, further comprising a dose indicating element comprising a stop that is moved away from a mating stop during a dose setting operation, and is moved toward the mating stop during a dose decreasing operation or when the actuation element is actuated.

19. The device according to claim 18, wherein the dose indicating element is at least rotationally decoupled from the rotary member during the dose setting and dose decreasing operations.

20. The device according to claim 18, wherein upon actuation of the actuating member, the dose indicating element is coupled to the rotary member such that rotation of the rotary member causes the dose indicating element to be moved toward the mating stop.

21. The device of claim 1, wherein during a dose setting operation, a dosing element is rotationally decoupled from the spring.

22. The device of claim 1, wherein the spring is configured as a compression spring and is supported on the propulsion member and the abutment.

23. A driving and dosing device for an injection device for administering a liquid product, comprising:
- a housing comprising an abutment;
- an actuating member displaceable relative to the housing to initiate a product dispensing;
- a propulsion member movable relative to the abutment in a dispensing direction in order to effect the product dispensing;
- a spring operable between the propulsion member and the abutment, the spring preloaded in a delivery state of the device and having sufficient energy that it can dispense a maximum dispensable product quantity from a product container within the device;
- a rotary member rotatable relative to the housing to cause the spring to move the propulsion member in the dispensing direction; and
- a clutch, wherein the clutch is opened upon actuating the actuating member such that the clutch releases the rotary member to cause rotation of the rotary member relative to the housing in a first rotational direction, and
- wherein the actuating member is coupled to the rotary member via a transmission mechanism that converts, during actuation of the actuating member, movement of the actuating member along the longitudinal axis into a rotary movement of the rotary member while the clutch is in a closed position.

* * * * *